US012655405B2

(12) United States Patent
Marraffini et al.

(10) Patent No.: US 12,655,405 B2
(45) Date of Patent: Jun. 16, 2026

(54) SEQUENCE SPECIFIC DEGRADATION OF SINGLE-STRANDED POLYNUCLEOTIDES WITH CARD1 NUCLEASE

(71) Applicant: The Rockefeller University, New York, NY (US)

(72) Inventors: Luciano Marraffini, Brooklyn, NY (US); Jakob Rostol, New York, NY (US)

(73) Assignee: THE ROCKEFELLER UNIVERSITY, New York, NY (US)

( * ) Notice: Subject to any disclaimer, the term of this patent is extended or adjusted under 35 U.S.C. 154(b) by 507 days.

(21) Appl. No.: 18/006,251

(22) PCT Filed: Jul. 19, 2021

(86) PCT No.: PCT/US2021/042251
§ 371 (c)(1),
(2) Date: Jan. 20, 2023

(87) PCT Pub. No.: WO2022/020270
PCT Pub. Date: Jan. 27, 2022

(65) Prior Publication Data
US 2023/0287371 A1      Sep. 14, 2023

Related U.S. Application Data

(60) Provisional application No. 63/120,565, filed on Dec. 2, 2020, provisional application No. 63/054,157, filed on Jul. 20, 2020.

(51) Int. Cl.
*C12N 9/22*      (2006.01)
*C12N 15/11*      (2006.01)

(52) U.S. Cl.
CPC ................ *C12N 9/22* (2013.01); *C12N 15/11* (2013.01); *C12N 2310/20* (2017.05)

(58) Field of Classification Search
CPC ...... C12N 9/22; C12N 15/11; C12N 2310/20; C12N 15/113
See application file for complete search history.

(56) References Cited

PUBLICATIONS

GenBank accession No. WP_013702306, Jun. 3, 2018.*
Witkowski et al., Biochemistry 38:11643-11650, 1999.*
Tang et al., Phil Trans R Soc B 368:20120318, 1-10, 2013.*
Seffernick et al., J. Bacteriol. 183(8):2405-2410, 2001.*
Singh et al., Current Protein and Peptide Science 19(1):5-15, 2018.*
Sadowski et al., Current Opinion in Structural Biology 19:357-362, 2009.*
UNIPROTKB Accession No. F2NWD3_TRES6, Uncharacterized protein, May 31, 2011, uniprot.org/uniprot/F2NWD3.txt?version= 35, 2 pages.
Han, C., et al., Complete genome sequence of Treponema succinifaciens type strain (6091T), Standards in Genomic Sciences, 2011, vol. 4, pp. 361-370.
Esvelt, K.M., et al., Orthogonal Cas9 Proteins for RNA-Guided Gene Regulation and Editing, Nat Methods, Nov. 2013, vol. 10, No. 11, pp. 1116-1121.
GENBANK Accession No. EMB32451, CRISPR-associated protein cas9/csn1, subtype II/nmemi [Treponema denticola MYR-T], Feb. 7, 2013, ncbi.nlm.nih.gov/protein/EMB32451.1, 2 pages.
Rostol, J.T., et al., The Card1 nuclease provides defence during Type III CRISPR immunity, Nature, Jan. 18, 2021, vol. 590, No. 7847, pp. 624-629.
Gootenberg, J.S., et al., Multiplexed and portable nucleic acid detection platform with Cas13, Cas12a, and Csm6, Science, Apr. 27, 2018, vol. 360, No. 6387, pp. 439-444.
Kellner, M.J., et al., SHERLOCK: Nucleic acid detection with CRISPR nucleases, Nat Protoc., Oct. 2019, vol. 14, No. 10, pp. 2986-3012.
Database UniProt, "RecName: Full=Card1 domain-containing protein {ECO:0000259|Pfam:PF09002};", Nov. 7, 2018.

* cited by examiner

*Primary Examiner* — Delia M Ramirez
(74) *Attorney, Agent, or Firm* — Hodgson Russ LLP

(57)      ABSTRACT

Provided is an isolated or recombinantly expressed protein comprising the sequence of SEQ ID NO: 1 (CARD1), or an amino acid sequence that is at least 90% identical to the sequence of CARD1. Methods for producing and isolating the CARD1 protein are provided. Also provided are methods that include using CARD1, CasIO and RNA obtained from a biological sample, and a guide RNA targeted to an RNA polynucleotide that may be in the biological sample, and determining whether or not the CARD1 cleaves a reporter ssDNA or reporter ssRNA that is added to the sample, to determine the presence or absence of the RNA polynucleotide. Kits for use in the assay are also provided.

2 Claims, 12 Drawing Sheets
Specification includes a Sequence Listing.

SEQUENCE SPECIFIC DEGRADATION OF SINGLE-STRANDED POLYNUCLEOTIDES WITH CARD1 NUCLEASE

CROSS-REFERENCE TO RELATED APPLICATIONS

This application claims priority to U.S. provisional application No. 63/120,565, filed on Dec. 2, 2020, and to U.S. provisional application No. 63/054,157 filed on Jul. 20, 2020, the disclosures of each of which are incorporated herein by reference.

STATEMENT REGARDING FEDERALLY SPONSORED RESEARCH OR DEVELOPMENT

This invention was made with government support under Grant No. DP1GM128184 awarded by the National Institutes of Health. The Government has certain rights in the invention.

FIELD OF THE INVENTION

This disclosure generally relates to the field of CRISPER/CAS systems, and more particularly to Cas1 systems, and diagnostic methods using a Cas1 nuclease, optionally in conjunction with a Cas10 protein, and specifically to a CARD1 protein.

BACKGROUND OF THE DISCLOSURE

Clustered, regularly interspaced short palindromic repeat (CRISPR) loci consist of repetitive DNA sequences intercalated with "spacer" sequences that match the genomes of viruses and plasmids that infect bacteria and archaea (1, 2). These loci are transcribed and processed to generate short RNA guides that contain the spacer sequence, known as the CRISPR RNA (crRNA) (3). Different effector complexes, encoded by the CRISPR associated (cas) genes, use the crRNA guides to find and destroy the nucleic acids of the invader (4). Depending on their cas gene content, CRISPR-Cas systems can be classified into six different types (5). Of these, type III systems display the most elaborate targeting mechanism. The crRNA in the type III Cas10 effector complex recognizes complementary invader's transcripts (6, 7), resulting in the activation of two catalytic domains within Cas10. The HD domain initiates single-stranded DNA (ssDNA) cleavage near the target transcription site (7, 8); i.e. within the genome of the invader. At the same time the Palm domain converts ATP into 3'-5' cyclic oligoadenylate (cA) of various sizes, commonly $cA_4$ and $cA_6$ (9, 10). These molecules function as secondary messengers that bind the CRISPR-Cas Associated Rossmann Fold (CARF) domain of Csm6 (11) or Csx1 (12), accessory RNases often found in type III-A or III-B loci, respectively. Binding of cA to the CARF domain activates an RNase domain, through which Csm6 degrades host and invader transcripts non-specifically, inducing a growth arrest essential for the type III-A CRISPR-Cas immune response against targets that are transcribed either weakly (13, 14) or late in the viral infection cycle (15).

Recent bioinformatics studies revealed the existence of a great diversity of genes associated with type III CRISPR-cas loci (16, 17). Many of them contain CARF domains fused to different effector domains with predicted catalytic or regulatory functions (18). Biochemical and structural analysis determined that one such protein, *Thermus thermophilus*

Can1, is activated by $cA_4$ binding to introduce nicks only in supercoiled DNA (19). However, whether and how these type III-associated, CARF-containing proteins, can be activated to provide immunity to prokaryotes remains to be demonstrated. Thus, there is an ongoing and unmet need to determine the characteristics of such proteins, and how they can be used to enhance and develop methods of using them. The present disclosure is pertinent to this need.

SUMMARY

The present disclosure provides an isolated or recombinantly expressed protein comprising the sequence of SEQ ID NO:1, or an amino acid sequence that is at least 90% identical to the sequence of SEQ ID NO:1, such proteins referred to herein as "CARD1." In embodiments, the isolated or recombinantly expressed protein comprising the sequence of CARD1 comprises additional amino acids that are not part of the CARD1 sequence, including but not necessarily limited to a purification tag. In non-limiting embodiments, the purification tag comprises a FLAG tag, a poly-histidine tag, such as 3-6 Histidine residues, a SUMO tag, GST, and the like. In embodiments, the protein may be biotinylated or conjugated to streptavidin. The disclosure also provides that the CARD1 protein is present within a cell that is not *Treponema succinifaciens*. In embodiments, the disclosure provides a cDNA encoding the CARD1 protein, including but not necessarily limited to a codon-optimize cDNA for expression in a particular organism; an expression vector encoding the CARD1 protein; and one or more cells comprising the expression vector encoding the CARD1 protein.

In embodiments, the disclosure provides a method comprising expressing the CARD1 protein in cells and separating the CARD1 protein from the cells. Also provided is a method comprising introducing into one or more cells the CARD1 protein, or an expression vector encoding the CARD1 protein. In embodiments, if the protein is expressed by the expression vector, expression of the protein from the expression vector may be controlled by an inducible promoter. In embodiments, the CARD1 protein degrades ssDNA, ssRNA, or a combination thereof. The disclosure also includes a method comprising including a CARD1 protein in an assay comprising Cas10 and RNA from a biological sample, and a guide RNA targeted to an RNA polynucleotide that may be in the biological sample, and determining whether or not the CARD1 cleaves a reporter ssDNA or reporter ssRNA that is added to the sample. If an RNA polynucleotide to which the guide RNA is present is in the sample, the method further comprises detecting a detectable signal produced at least in part by CARD1 cleavage of the reporter ssDNA or ssRNA. In embodiments, the RNA polynucleotide to which the guide RNA is specific is present in the assay comprises a viral mRNA, a viral genomic RNA, a viral subgenomic RNA, or a combination thereof. In embodiments, the described assay is comprised by a container, or a lateral flow device. In embodiments, the presence of viral RNA is detected, and the method further comprises administering to the individual from whom the biological sample was obtained an anti-viral agent, and/or one or more antibodies that bind with specificity to the virus.

In another embodiment, the disclosure provides a kit. The kit comprises an isolated or recombinantly produced CARD1 protein, and may further comprise at least one of: a detectably labeled ssDNA, a detectably labeled ssRNA, a Cas13 and/or Cas10 protein, a buffer suitable for function of the CARD1 protein, or instructions for using the CARD1 protein in an assay. The buffer may also comprise Manganese (Mn) and/or Cyclic Tetra-Adenylate (cA₄).

In another embodiment, the disclosure provides an in vitro method comprising degrading ssDNA and/or ssRNA with a CARD1 protein, wherein the method may further comprise use of a Cas10 protein. An in vitro composition, which may be a cell free composition, comprising a CARD1 protein and a ssDNA or a ssRNA template is also provided. The composition may also comprise cA₄ and/or Mn. In embodiments, Cas10 protein, a Cas13 protein, or a combination thereof, may also be present in the described composition.

BRIEF DESCRIPTION OF THE FIGURES

For a fuller understanding of the nature and objects of the disclosure, reference should be made to the following detailed description taken in conjunction with the accompanying figures.

DETAILED DESCRIPTION OF THE DISCLOSURE

Figure 1:
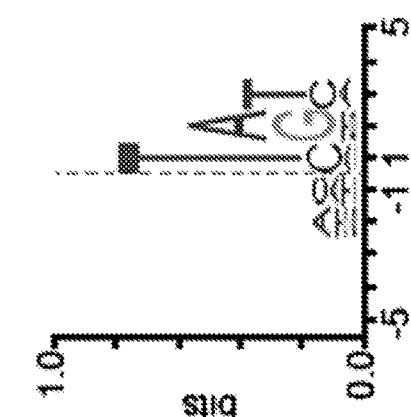
FIG. 1. CARD1 is a cA4-activated single-stranded DNase. (a) CARD1 digestion of ΦX174 ssDNA in the presence of cA4, cA6 and/or MnCl2, visualized by agarose gel electrophoresis. (b) CARD1 digestion of M13 ssDNA like specified, visualized by agarose gel electrophoresis. (c) Cleavage preference of CARD1, represented as a WebLogo, determined after next generation sequencing of ΦX174 degradation products. Five nucleotide positions upstream (−5 to −1) and downstream (1 to 5) of the detected cleavage sites are shown. (d) like (b), but with ΦX174 supercoiled dsDNA, (e) like (b) but with ΦX174 linearized dsDNA.
Figure 1:
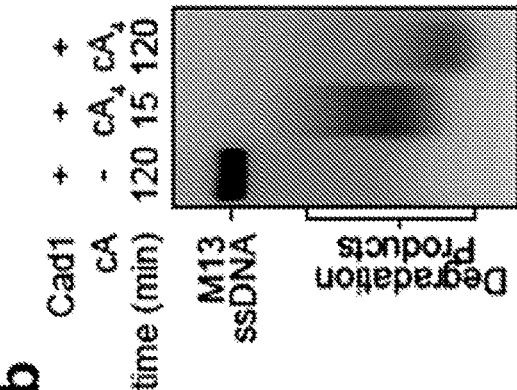
Figure 1:
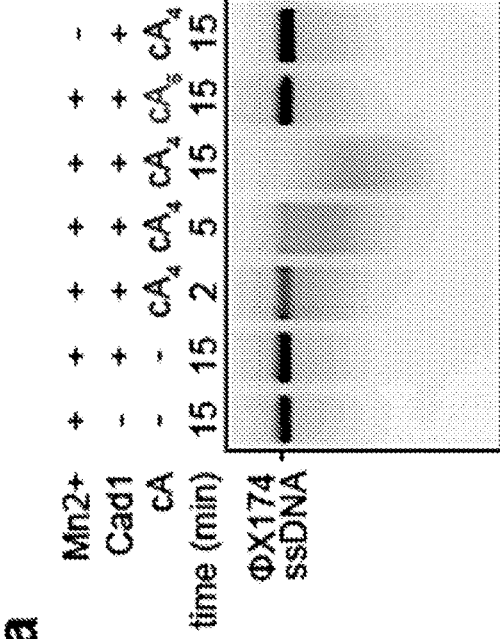
Figure 1:
Figure 1:
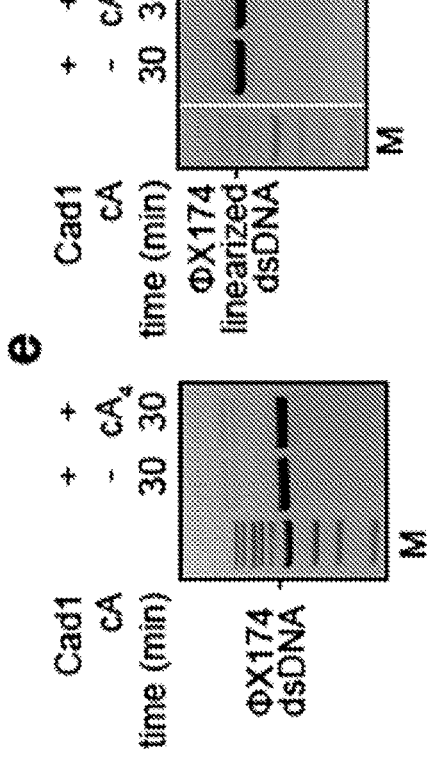

Although claimed subject matter will be described in terms of certain embodiments/examples, other embodiments/examples, including embodiments/examples that do not provide all of the benefits and features set forth herein, are also within the scope of this disclosure. Various structural, logical, and process step changes may be made without departing from the scope of the disclosure.

Every numerical range given throughout this specification includes its upper and lower values, as well as every narrower numerical range that falls within it, as if such narrower numerical ranges were all expressly written herein. All ranges provided herein include all values that fall within the ranges to the tenth decimal place, unless indicated otherwise.

Throughout this application, the singular form encompasses the plural and vice versa. All sections of this application, including any supplementary sections or figures, are fully a part of this application.

All of the nucleotide and amino acid sequences associated with the GenBank or other database accession numbers are incorporated herein by reference as they exist on the filing date of this application or patent. The disclosure includes amino acid sequences that are from 80%-99% similar to those amino acid sequences described herein, and includes amino acid sequences that include insertions and deletions. The disclosure also includes all polynucleotide sequences of the CARD1 nuclease (previously referred to as CARD1 nuclease) and all sequences complementary to those sequences.

Examples of nucleotide and amino acid sequences encoding the CARD nuclease are as follows.
CARD1 (Gene Tresu_2185) Nucleotides Sequence (Codon Optimized):

```
                              (SEQ ID NO: 2)
ATGAAAGAGACTATTTTGGTTAACTTGGTTAGTGAGCAAACAATTCCTA

ATGTACAATTTATCAAGTGGTACTTTAATAAAAAGCAAACACCAATGAA

GATATTGTTAGTGAGTACTAAGGAGATGGAACAGAAAGAAAAATCATTG

TTCATCAAGAACGCTTTACACTTTTCAGATTCATTCGTGGAGTGGGAGA

CAATTCACACTGACGGAAACGACATATCAAAGACAGAAAATATTTTGAC

AGACTATTTCAGAGATAATGAATACAAAAATATAATAGTTAATATTACG
```

```
-continued
GGCGGTACAAAGATCATGTCTTTAGCAGCATTTGATTTCTTTAATAACA

AACCTAACACAGAGATATTCTACCAACCTATAGGTAAAGAATTGCAGGA

GTTATACCCAAATAAGCAAAAGTACGACATGTTCGAAGTGTTATCTTTA

AAGGAATATTTGGATGCGCATGGTATTAGTTATAAATACGATAACGAGT

GTGTCAAAGACTGGAACTATAATAAGACGGTATATGATTTGTGCGTTGC

GGACAATCGTGAATTAATAAAGGGCATGATCGCTTTGCAGAACAACTCA

TATTTCAACAATGTATATAAGCGAAAAGATTTTTTAGACTTTACTCAGA

TTGAGGAGGAGAAGTTCATTGCTATCAATCATCCAGCGGCTACAAAGGA

GAATATGATTAAGATCTTACAAATATTTGGATTTGATGTTAGTCGAATT

GAGCACAAGCACATCCGTTATATAACTGGCGGTTGGTTCGAGGAGTATG

TATATCAGAAAATTTGCAATGAATACCATAACGTCGATGAAAAGAACGT

AGCGTTAAACGTTACAATTCAGAAGGGAAATGACAAAAACGAGTTGGAT

GTTATCTACTTGGACAAAGACAATAAGTTACACGTGATAGAATGTAAGA

GTTTCGTCGATGGAAACGAAGGCAACAGAGTATTGAACGACGCGTTATA

TAAGTTACAAGCGATCATCAAGAGTAAGTTCGGATTATATGTAAAGCAA

CACTTGTATACGAAAAGTATTATAGAAAAAGAAACTCCATTGAACAGAG

CTAAAGAGTTTGGAATTGACATTAAAGACGGTACACAATTA TGA
```

(italics indicates stop codon)
CARD1 (Gene Tresu_2185) Amino Acid Sequence:

```
                              (SEQ ID NO: 1)
MKETILVNLVSEQTIPNVQFIKWYFNKKQTPMKILLVSTKEMEQKEKSL

FIKNALHFSDSFVEWETIHTDGNDISKTENILTDYFRDNEYKNIIVNIT

GGTKIMSLAAFDFFNNKPNTEIFYQPIGKELQELYPNKQKYDMFEVLSL

KEYLDAHGISYKYDNECVKDWNYNKTVYDLCVADNRELIKGMIALQNNS

YFNNVYKRKDFLDFTQIEEEKFIAINHPAATKENMIKILQIFGFDVSRI

EHKHIRYITGGWFEEYVYQKICNEYHNVDEKNVALNVTIQKGNDKNELD

VIYLDKDNKLHVIECKSFVDGNEGNRVLNDALYKLQAIIKSKFGLYVKQ

HLYTKSIIEKETPLNRAKEFGIDIKDGTQL
```

Functional fragments of CARD1/SEQ ID NO:1 are included in the disclosure.

In an aspect, this disclosure provides compositions comprising the CARD1 nuclease. In embodiments, an in vitro method is provided, wherein an isolated or recombinantly produced CARD1 is used to degrade single stranded DNA, for any purpose. The same applies to Cas10. In embodiments, the CARD1 protein is used in a complex with a Cas10 protein.

In a non-limiting embodiment, the CARD1 nuclease (which may include any suitable Cas10 protein) is used in an adaptation of a nucleic acid diagnostic assay known in the art as SHERLOCK (for Specific High Sensitivity Enzymatic Reporter UnLOCKing) assay, described in PCT publication WO2017219027, published Dec. 21, 2017, and SHERLOCK: nucleic acid detection with CRISPR nucleases, Kellner M J, Koob J G, Gootenberg J S, Abudayyeh O O, and Zhang F. Nature Protocols. 2019, October; 14(10):2986-3012. doi: 10.1038/s41596-019-0210-2. (NATURE PROTOCOLS, VOL 14, OCTOBER 2019, 2986-3), the disclosures of each of which are incorporated herein by reference.

The SHERLOCK assay is used to detect and/or quantify a target RNA or using a CRISPR Cas related approach. In the known SHERLOCK assay, a detectably labeled non-target RNA is used to provide a means of diagnostic readout using Cas13 in guide RNA programmed recognition of, for example, a polynucleotide target. Embodiments of the disclosure include recognition of DNA and RNA polynucleotides. Using RNA and Cas13 as an example, if the RNA target (e.g., an RNA that signifies the presence of a virus or other cell that expresses the target RNA), Cas13 complexes with the target RNA in the sample, and the non-specific Cas13 RNA nuclease activity of Cas13 results in enzymatic degradation of a detectably labeled RNA (e.g., a reporter RNA) that, for example, comprises a detectable label and a quencher. For instance, the detectably labeled RNA may comprise a fluorophore and a quencher moiety conjugated to the reporter RNA in sufficient proximity to one another such that the detectable signal is quenched when the RNA is intact. Accordingly, when and if the RNA reporter is cleaved by the non-specific nuclease activity of the Cas13, which is considered to only become active once the Cas13 has engaged a target in a guide-RNA directed manner, the detectable label is liberated from the intact reporter RNA, and a signal from it can be detected using any suitable approach. The present disclosure provides for use of CARD1 in the conventional SHERLOCK assay, and also for substitution of the reporter RNA in an adaptation of the SHERLOCK assay using a similarly labeled reporter polynucleotide, but wherein the reporter polynucleotide is a single stranded (ss) DNA reporter. Thus, the CARD1 nuclease will degrade the ss reporter and produce a detectable signal in the same manner as in the SHERLOCK assay, whether or not the ss polynucleotide is RNA or DNA. The function of CARD1 is facilitated by its interaction with Cas10. In embodiments, the CARD1 or functional fragment of it is provided together with Cas10 or a functional fragment of Cas10. In embodiments, CARD1, and/or a combination of a CARD1 and Cas10 is used. In embodiments, a combination of CARD1 and Cas10 can be substituted for Cas13 in the known SHERLOCK assay.

A representative Cas10 amino acid sequence is as follows:

```
                                      (SEQ ID NO: 3)
MNKKNILMYGSLLHDIGKIIYRSGDHTFSRGTHSKLGHQFLSQFSEFKD

NEVLDNVAYHHYKELAKANLDNDNTAYITYIADNIASGIDRRDIIEEGD

EEYEKQLFNFDKYTPLYSVFNIVNSEKLKQTNGKFKFSNESNIEYPKTE

NIQYSSGNYTTLMKDMSHDLEHKLSIKEGTFPSLLQWTESLWQYVPSST

NKNQLIDISLYDHSRITCAIASCIFDYLNENNIHNYKDELFSKYENTKS

FYQKEAFLLLSMDMSGIQDFIYNISGSKALKSLRSRSFYLELMLEVIVD

QLLERLELARANLLYTGGGHAYLLVSNTDKVKKKITQFNNELKKWFMSE

FTTDLSLSMAFEKCSGDDLMNTSGNYRTIWRNVSSKLSDIKAHKYSAED

ILKLNHFHSYGDRECKECLRSDIDINDDGLCSICEGIINISNDLRDKSF

FVLSETGKLKMPFNKFISVIDYEEAEMLVQNNNQVRIYSKNKPYIGIGI

STNLWMCDYDYASQNQDMREKGIGSYVDREEGVKRLGVVRADIDNLGAT

FISGIPEKYNSISRTATLSRQLSLFFKYELNHLLENYQITAIYSGGDDL

FLIGAWDDIIEASIYINDKFKEFTLDKLTLSAGVGMFSGKYPVSKMAFE

TGRLEEAAKTGEKNQISLWLQEKVYNWDEFKKNILEEKLLVLQQGFSQT
```

-continued

```
DEHGKAFIYKMLALLRNNEAINIARLAYLLARSKMNEDFTSKIFNWAQN

DKDKNQLITALEYYTYQIREAD
```

A representative Cas10 nucleotide coding sequence is as follows:

```
                                      (SEQ ID NO: 4)
ATGAATAAAAAAAATATATTAATGTATGGCTCTTTATTACATGATATAG

GGAAAATTATATATCGAAGTGGTGATCATACATTTTCAAGAGGTACGCA

TTCAAAATTAGGTCATCAATTTTTGTCCCAATTTTCAGAATTTAAAGAC

AACGAAGTGCTTGATAACGTTGCTTATCATCATTACAAAGAACTCGCAA

AAGCTAATTTAGATAATGATAATACAGCTTATATTACCTATATTGCGGA

TAATATTGCGAGTGGTATTGATAGAAGAGATATTATAGAAGAAGGCGAT

GAAGAATACGAAAAACAACTATTTAATTTTGATAAATATACACCGCTAT

ATAGTGTGTTTAATATTGTGAATTCTGAAAAATTGAAACAAACAAACGG

GAAGTTTAAATTTTCTAATGAAGTAATATTGAATATCCTAAAACTGAA

AACATTCAATATTCAAGTGGAAATTATACAACATTAATGAAAGATATGA

GTCATGATTTAGAGCACAAATTAAGTATTAAAGAAGGTACATTTCCTTC

ATTATTACAATGGACGGAAAGTCTATGGCAATATGTACCTAGTTCGACA

AATAAAAACCAATTAATTGATATTTCTCTTTATGATCATAGTCGTATTA

CATGTGCCATCGCCAGTTGTATATTTGATTATTTAAATGAAAATAACAT

ACATAATTACAAAGATGAATTGTTCTCAAAGTATGAAAATACCAAATCA

TTTTATCAAAAAGAAGCTTTTTTACTACTTAGTATGGATATGAGTGGTA

TTCAAGATTTTATTTACAATATAAGCGGTTCTAAAGCATTAAAGAGTCT

AAGATCTCGTAGTTTTTATTTAGAACTCATGCTTGAAGTAATCGTTGAT

CAATTATTAGAAAGATTAGAATTAGCACGAGCAAATCTTTTGTATACAG

GTGGTGGCCATGCTTATTTATTAGTGTCTAATACTGATAAAGTGAAGAA

AAAAATAACTCAATTTAATAATGAATTAAAAAAATGGTTTATGTCAGAA

TTTACTACAGATCTTTCATTATCAATGGCTTTTGAAAAATGTAGTGGCG

ATGATTTAATGAATACAAGTGGTAATTATAGAACTATTTGGCGTAATGT

TAGCAGCAAACTTTCTGATATTAAAGCGCATAAATATTCCGCGGAAGAT

ATATTAAAATTAAATCATTTTCATTCGTATGGAGATCGGGAATGTAAAG

AATGTTTAAGAAGTGACATAGATATTAATGATGATGGACTATGTAGTAT

ATGTGAAGGAATTATTAATATATCAAATGATTTAAGAGATAAATCATTC

TTTGTACTGTCAGAAACTGGAAAATTAAAAATGCCATTCAATAAATTTA

TATCGGTTATTGATTATGAAGAGGCAGAAATGTTAGTACAAAATAATAA

TCAAGTTCGTATTTACAGTAAAAATAAACCATATATAGGCATAGGAATA

TCAACAAATTTATGGATGTGTGATTACGACTATGCTAGTCAAAATCAAG

ATATGAGAGAAAAAGGTATTGGAAGTTATGTAGATAGAGAAGAAGGGGT

TAAGCGTTTAGGCGTGGTACGTGCCGATATAGATAATCTCGGTGCTACA

TTTATATCTGGAATTCCAGAAAAAATATAATTCAATTTCAAGAACAGCTA

CATTGTCTCGTCAATTATCATTATTTTTTAAATACGAATTAAATCATTT
```

-continued

```
ATTAGAAAATTATCAAATTACTGCTATATATTCAGGCGGTGACGATTTA

TTTTTAATCGGTGCATGGGATGACATTATAGAAGCAAGCATTTATATAA

ATGACAAATTTAAAGAGTTTACTCTTGATAAACTAACATTGTCTGCCGG

GGTTGGAATGTTTAGTGGTAAGTACCCAGTTTCTAAAATGGCTTTTGAG

ACAGGACGACTTGAAGAAGCGGCTAAGACTGGTGAAAAAAATCAGATAT

CTCTTTGGTTACAAGAAAAAGTATATAACTGGGATGAGTTTAAAAAGAA

TATCTTAGAAGAAAAACTTCTCGTTTTACAACAGGGGTTTTCTCAAACA

GATGAACACGGGAAAGCCTTCATTTATAAAATGCTCGCTTTACTGAGAA

ATAATGAAGCTATTAATATTGCTCGTTTAGCTTACTTATTAGCAAGAAG

CAAGATGAATGAGGATTTTACGTCTAAAATTTTTAATTGGGCTCAAAAC

GACAAAGATAAAAATCAATTAATTACAGCGTTAGAGTATTATATTTATC

AAATAAGGGAGGCTGAT*TGA*
```

(italics indicates stop codon)

As described further herein, the CARD1 nuclease requires adenylate, which in one embodiment may be an oligoadenylate such as $cA_4$ to exhibit its ssDNA nuclease activity. In the adapted SHERLOCK assay, the degradation of poly-adenylated RNA can provide a source of a suitable adenylate, such as linear $cA_4$. Thus, if a sample that is tested in the adapted SHERLOCK assay of this disclosure contains a target RNA to which Cas13 (or alternatively a Cas10/CARD1 complex) binds in a gRNA directed manner, the non-specific RNA nuclease activity of Cas13, triggered by binding of the Cas13 to the target RNA, will provide a source of adenylate to allow degradation of the labeled ssDNA, yielding a detectable signal. Accordingly, the present disclosure provides compositions, methods, and kits for use in an adapted diagnostic assay. In embodiments, the kits, and the disclosure more generally, provides an isolated CARD1 enzyme, and may further comprise any suitable reagents for use in a diagnostic assay. In embodiments, the CARD1 enzyme may be provided with a detectably labeled ssDNA for use as a CARD1 substrate in the diagnostic assay.

In another aspect, the disclosure provides for use of a ssRNA substrate in a described assay, but wherein the assay is supplemented with manganese (Mn). Thus, the disclosure in various embodiments takes advantage of CARD1 by $cA_4$ activation, which allows the cleavage of ssDNA, ssRNA and both ssDNA and ssRNA, in a Mn cation-dependent manner.

In embodiments, a kit of this disclosure provides a recombinant or isolated CARD1 protein or functional fragment thereof, and may further comprise a recombinant or isolated Cas10 protein. In embodiments, the disclosure provide a fusion protein comprising amino acids from Cas10 and from CARD1. The kit may further comprise a detectably labeled ssDNA. The kit may comprise a suitable buffer, such as a buffer that contains Mn cations.

The disclosure further comprises the addition of an anti-CRISPR agent to, for example, enhance or prolong the time during which Cas13 is bound to an target RNA in a guide directed manner. In an embodiment, a suitable anti-CRISPR agent comprises a protein known as AcrVIA1, which has the following amino acid sequence:

```
                                        (SEQ ID NO: 5)
MIYYIKDLKVKGKIFENLMNKEAVEGLITFLKKAEFEIYSRENYSKYNK

WFEMWKSPTSSLVFWKNYSFRCHLLFVIEKDGECLGIPASVFESVLQIY
```

-continued

```
LADPFAPDTKELFVEVCNLYECLADVTVVEHFEAEESAWHKLTHNETEV

SKRVYSKDDDELLKYIPEFLDTIATNKKSQKYNQIQGKIQEINKEIATL

YESSEDYIFTEYVSNLYRESAKLEQHSKQILKEELN.
```

AcrVIA1 is known in the art from, for example, Meeske et al., *Science*, 2020 May 28; eabb6151. doi: 10.1126/science.abb615, the disclosure of which is incorporated herein by reference.

The disclosure includes adding CARD1 and Cas10 to a biological sample obtained from an individual that is either tested directly, or is processed before testing, such as to separate RNA from the sample. In embodiments, the CARD1 and the ss polynucleotide is added to a sample with a suitable Cas enzyme (e.g., Cas13 or Cas10) and a detectably labeled ss polynucleotide reporter, or is added a short time (e.g., within 1 second to 60 minutes) after the Cas enzyme in the sample has associated with the target ss polynucleotide reporter, if the target ss polynucleotide (e.g., RNA, in the detection of a ss virus) is present, in the patient sample. Compositions comprising a Cas enzyme, a guide RNA, a detectably labeled reporter ssDNA, and a CARD1 nuclease, and Cas10 proteins, as described herein, are encompassed by the disclosure. In embodiments, any detectable label can be used with the reporter ss polynucleotide, non-limiting examples of which include fluorophores, metals or chemiluminescent moieties, fluorescent particles, quantum dots, etc., provided the signal from the detectable label can be quenched, or its intensity shifted to a different wavelength in, for example, a fluorescence resonance energy transfer (FRET) process by a suitable quencher moiety conjugated to the reporter RNA.

In an aspect, this disclosure provides methods for using the described compositions for identifying the presence of RNA or DNA from any source, including but not limited to a bacteria or a virus, in a sample. In embodiments, the presence, absence, and or amount of RNA is determined. In embodiments, viral RNA is determined. In embodiments, the presence, absence, and/or amount of any polyadenylated RNA is determined. Thus, in embodiments, the present disclosure provides diagnostic methods, and kits for use in the diagnostic methods.

In a non-limiting embodiment, the disclosure provides for use of the CARD1 and Cas10 proteins for detecting RNA viruses, including but not limited to the coronavirus referred to in the art the time of this disclosure as SARS-CoV-2, which causes COVID-19. In an embodiment, the assay is performed using a lateral flow device. In embodiments, the testing is performed by testing for the presence or absence of RNA encoded by the viral S gene and/or the Orf1ab gene. In embodiments, the Cas13 used in this approach or related approaches is LwaCas13a. In embodiments, liberated label can be detected in the lateral flow device at a predetermined position. Suitable controls may be included, such as a predetermined amount of synthetically produced viral target RNA.

In alternative embodiments, the disclosure provides for determining the presence, absence and/or amount of DNA in a sample. In a non-limiting embodiment, the method is performed by transcription from a DNA template, wherein detection of the transcribed RNA acts as a surrogate for direct detection of DNA, although DNA can also be assayed as described herein.

In embodiments, a biological sample analyzed according to this disclosure comprises any suitable biological sample, including but not limited to blood, urine, mucosa, mucosal secretions, saliva, and lacrimal secretions. In embodiments, a biological sample is tested directly. In embodiments, the biological sample is subject to a processing step before testing, a non-limiting example of which comprises RNA extraction. In embodiments, a diagnostic assay of this disclosure may exhibit increased sensitivity to the presence or absence of a particular RNA. In embodiments, the CARD1 can be used for ribosome profiling by using CARD1 to digest segments of mRNA that are not protected from digestion by ribosomes.

While sequences or reference numbers have been provided for CARD1 and Cas10 proteins, it will be appreciated that proteins from other similar CRISPR/Cas systems also may be used. CARD1 and Cas10 proteins from other prokaryotic sources and nucleotides sequences encoding such proteins, that have at least 80%, at least 85%, at least 90%, at least 95%, at least 98%, at least 99%, or 100% identity with the sequences/references provided herein may be used. This disclosure encompasses variants of the CARD1 and Cas10 proteins, wherein a variant of the protein is at least 80%, 85%, 90%, 91%, 92%, 93%, 94%, 95%, 96%, 97%, 98% or 99% identical to the listed amino acid sequence. In this regard, as is known in the art, Cas10 is a complex, which is referred to as Cas10-Csm. Cas10-Csm contains a guide RNA that anneals a complementary target RNA and starts producing polyA and/or cyclic oligoA (cOA). This diffuses into the cytoplasm, where is bound by CARD1 to activate it.

In an aspect, the disclosure provides nucleic acid sequences encoding the full CARD1 nuclease (which may include Csm) and Cas10 protein and/or functional fragments or variants thereof as described herein. The nucleic acid sequence can encode an RNA molecule corresponding to the amino acid sequence of the CARD1 protein described above. In embodiments, the sequence which encodes a CARD1 or Cas10 protein or a variants thereof, as described herein may be at least 80%, 85%, 90%, 91%, 92%, 93%, 94%, 95%, 96%, 97%, 98% or 99% identical to the listed nucleic acid sequences. This also disclosure provides expression vectors comprising the sequences encoding CARD1 proteins as described herein. Methods for cloning expression vectors (CARD1 and Cas10 protein constructs), and methods for expressing and purifying recombinant bacterial proteins of the invention are well known in the art. For example, expression vectors of the present disclosure may be expressed in suitable cells such as, mammalian cells (e.g., murine and/or human cells), using retroviral, adenoviral, or lentiviral vectors. For generating CARD1 proteins, an expression construct encoding a bacterial protein(s) as described or referenced in this disclosure may be introduced into the cell by transfection or other appropriate method known in the art. Appropriate host cells include, but are not limited to, bacterial, yeast, insect, and mammalian cells. The host cells may then be lysed to extract the expressed bacterial protein(s) for subsequent purification and use, such as in a therapeutic composition.

The expression vector is not particularly limiting other than by a requirement for the CARD1 and/or Cas10 protein expression to be driven from a suitable promoter. Many suitable expression vectors and systems are commercially available. Non-limiting examples of vectors include plasmids. The expression vectors may be configured to produce CARD1 proteins such that they include suitable components that facilitate purification, such as HIS or FLAG tag, or improve solubility or secretion or other functions. In an embodiment, a CARD1 protein is provided with a nuclear localization signal.

A nucleic acid encoding a CARD1 protein construct may also be operably linked to a nucleotide sequence encoding a selectable marker. A selectable marker may be used to efficiently select and identify cells that have integrated the exogenous nucleic acids. Selectable markers give the cell receiving the exogenous nucleic acid a selection advantage, such as resistance towards a certain toxin or antibiotic. Suitable examples of antibiotic resistance markers include those coding for proteins that impart resistance to kanamycin, streptomycin, neomycin, gentamycin (G418), ampicillin, tetracycline, chloramphenicol, puromycin, hygromycin, zeocin, and blasticidin.

The present disclosure also provides pharmaceutical compositions comprising the CARD1 proteins as described herein. The compositions may comprise pharmaceutically acceptable diluents, preservatives, solubilizers, emulsifiers, and/or carriers. For example, pharmaceutical compositions may comprise various buffers (e.g., Tris-HCl, acetate, phosphate), additives such as detergents and solubilizing agents (e.g., Tween 80, Polysorbate 80), anti-oxidants (e.g., ascorbic acid, sodium metabisulfite), preservatives (e.g., Thimersol, benzyl alcohol) and bulking substances (e.g., lactose, mannitol). Such pharmaceutical composition components are known in the art See, e.g., Remington: The Science and Practice of Pharmacy (2005) 21st Edition, Philadelphia, PA Lippincott Williams & Wilkins. The materials may be incorporated into particulate preparations of polymeric compounds such as polylactic acid, polyglycolic acid, etc. or into liposomes. Hylauronic acid may also be used. Preparations for parenteral administration may include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain other adjuvants, preserving, wetting, emulsifying, and dispersing agents.

In embodiments, a composition comprising a CARD1 protein described herein can be used as a treatment for a disease or condition, such as a disease or condition that is associated with deleterious sDNA. The term "treatment" as used herein refers to alleviation of one or more symptoms or features associated with the presence of the particular condition or suspected condition being treated. Treatment does not necessarily mean complete cure or remission, nor does it preclude recurrence or relapses. Treatment can be effected over a short term, over a medium term, or can be a long-term treatment, such as, within the context of a maintenance therapy. Treatment can be continuous or intermittent. In embodiments, a CARD1 protein is used to inhibit phage infection and/or replication. Such an approach may be used, for example, in the food or beverage industries to combat deleterious phage infections where bacteria are used in the preparation of food or beverages, and/or wherein the bacteria are a component of a food or beverage, including but not necessarily limited to dairy products such as yogurts, and fermented foods and beverages.

The term "therapeutically effective amount" as used herein refers to an amount of an agent sufficient to achieve, in a single or multiple doses, the intended purpose of treatment. The exact amount desired or required will vary depending on the particular compound or composition used, its mode of administration, patient specifics and the like. Appropriate effective amount can be determined by one of ordinary skill in the art informed by the instant disclosure using only routine experimentation.

The present compositions may be administered to an individual in need thereof using any suitable route including parenteral, subcutaneous, intraperitoneal, intrapulmonary, and intranasal, and, if desired for local treatment, such as, intratumoral administration. Parenteral infusions include intramuscular, intravenous, intraarterial, intraperitoneal, intradermal, or subcutaneous administration.

The following examples are meant to illustrate, and are not intended to be limiting.

Example 1

Figure 2:
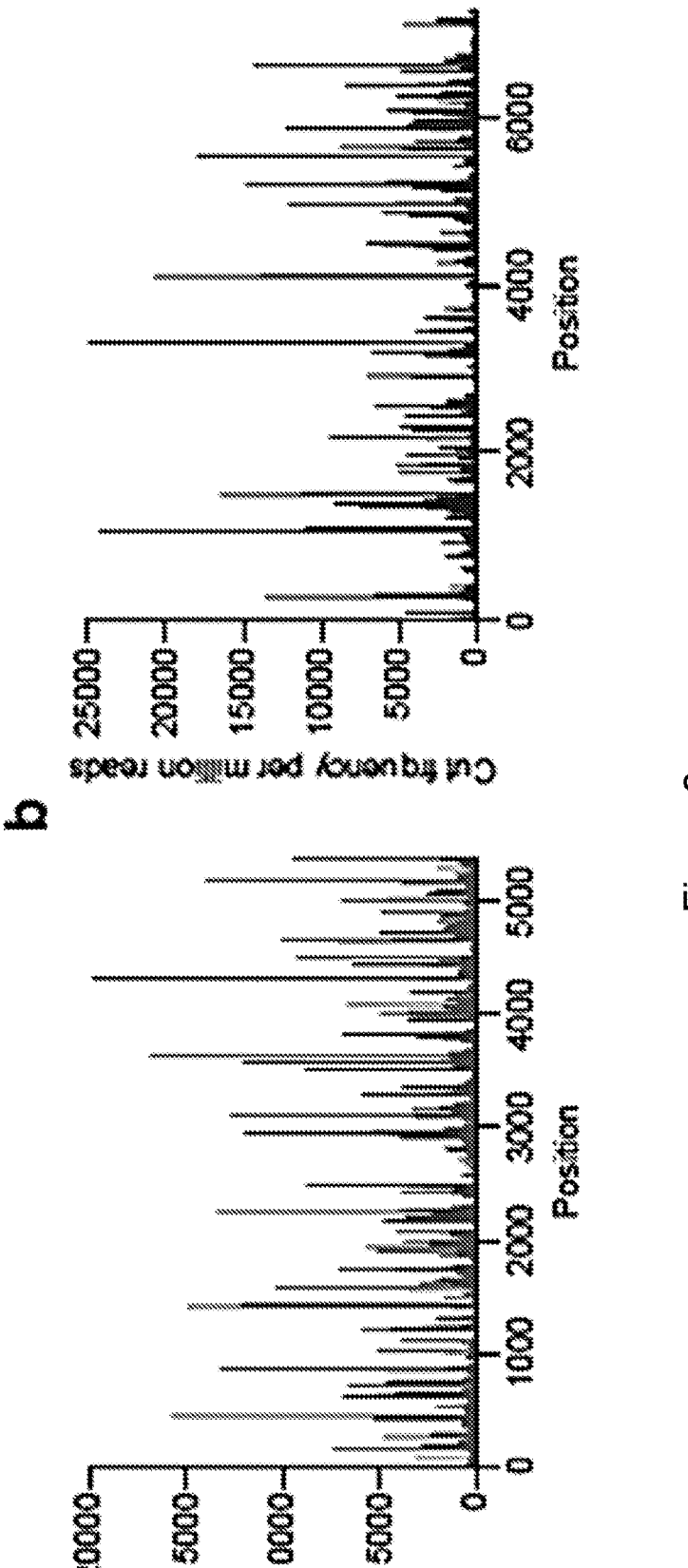
FIG. 2. Patterns of CARD1 cleavage. (a) Overview of CARD1 cleavage sites across the ΦX174 genome, based on the 5' end mapping of DNA degradation products obtained from the 2 hours timepoint in FIG. 1a, per 1 million reads. There appears to be preferential cleavage sites that may reflect lack of CARD1 access to secondary structures formed within the ssDNA molecule. 26.7% of cuts occur at the 25 most frequent positions. (b) Same as (a) but after the analysis of M13 ssDNA degradation products. 31.1% of cuts occur at the 25 most frequent positions. (c) Fragment size distribution of the ΦX174 degradation products from the 2 hours timepoint in FIG. 1a. The average fragment length (163.6 nucleotides) is marked by the dotted line. (d) Same as (c) but analyzing M13 degradation products. The average fragment length (150.1 nucleotides) is marked by the dotted line. (e) Cleavage preference of CARD1, represented as a WebLogo, determined after NGS of M13 degradation products. Five nucleotide positions upstream (−5 to −1) and downstream (1 to 5) of the detected cleavage sites are shown.
Figure 2:
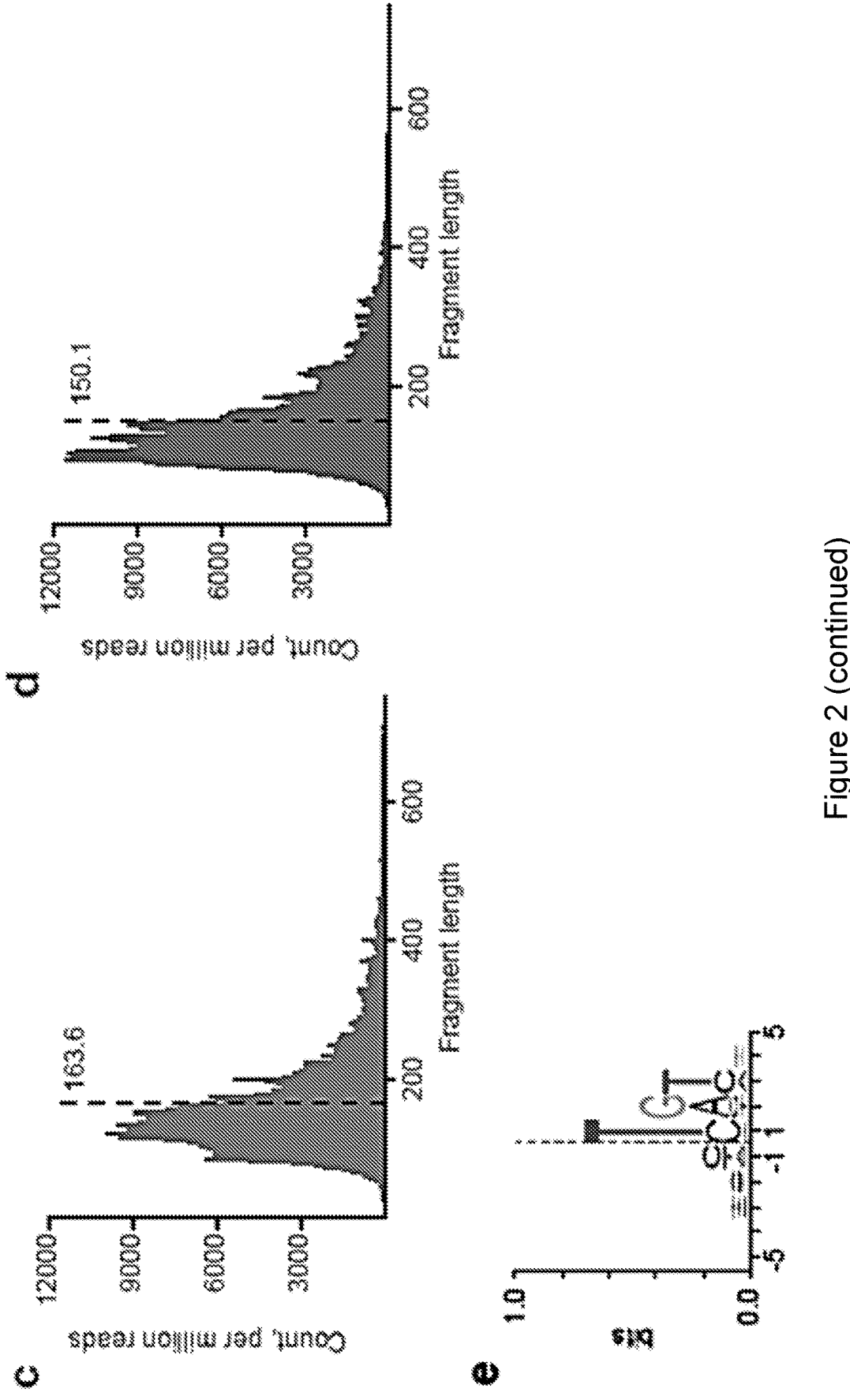

To investigate this, we characterized Tresu_2185, found in the type III-A CRISPR-cas locus of the mesophilic gram-negative spirochete *Treponema succinifaciens* (18). Tresu_2185 contains 373 amino acids (43.9 kDa), is a member of the Pfam family pfam09002 (domain of unknown function 1887, DUF1887), and is composed of an N-terminal CARF domain and a C-terminal restriction endo-nuclease-like (REase) domain, typically found in type II restriction endonucleases or Holliday junction resolvases (20), where the two acidic residues coordinate a divalent cation important for catalysis. To evaluate the biochemical activity of Tresu_2185, we expressed and purified it from *Escherichia coli*, and incubated with different nucleic acids and cAs. We found that the addition of $cA_4$, but not $cA_6$, resulted in the degradation of circular $\Phi$X174 and M13 ssDNA (FIGS. 1a, b), but $cA_4$ did not promote cleavage of supercoiled or linearized $\Phi$X174 dsDNA (FIGS. 1d, e). Degradation required the addition of Mn cation (FIG. 1a) and resulted in a smear of products, suggesting that ssDNA cleavage is not specific. These results demonstrate that Tresu_2185 is a $cA_4$-activated, non-specific ssDNA nucle-ase. Therefore, we renamed it cA-activated DNase and RNase 1, or CARD1. Next generation sequencing of the $\Phi$X174 and M13 ssDNA degradation products showed cleavage across both genomes (FIGS. 2a, b), with an aver-age product size of ~150 nucleotides (FIGS. 2c, d), prefer-entially upstream of T(A/G) sites (FIGS. 1c, 2e).

Figure 3:
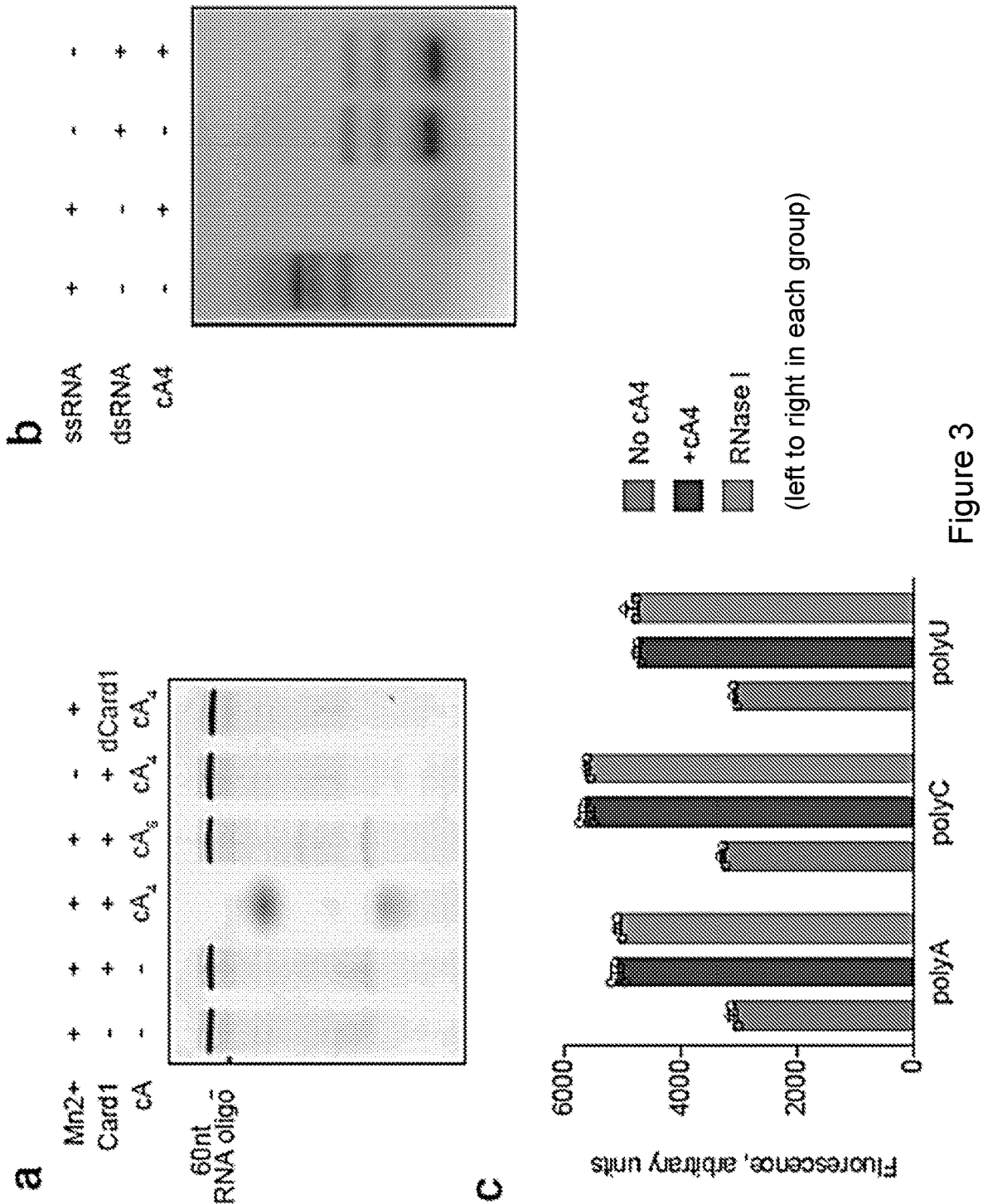
FIG. 3. CARD1 is able to degrade ssRNA in vitro. (a) CARD1 is incubated with a 60 nucleotide ssRNA oligo fluorescently labelled with Cy3 for 15 minutes. The RNase activity is activated by cA4, but not cA6, requires Mn2+, and the activity is abrogated upon mutation of the CARD1 catalytic site (dCARD1). (b) Incubating CARD1 with either a ssRNA ladder, or a dsRNA ladder, for 15 minutes, shows that CARD1 is specific for ssRNA. (c) CARD1 or RNase I was incubated with short RNA oligos with either 15 adenines, cytosines, or uracils, with a 5' fluorophore and a 3' quencher. The increase in fluorescent signal results from successful linker cleavage, demonstrating that CARD1 can cut next to all three bases. Guanines could not be tested since multiple guanines form structures resistant to digestion.

Further biochemical experiments established that in addi-tion to being a DNase, CARD1 is able to degrade RNA. Incubating CARD1 with a 60 nucleotide RNA oligo dem-onstrated that the RNA is degraded in the presence of $cA_4$, but not $cA_6$ (FIG. 3a). Single-stranded RNA, but not double-stranded RNA, was degraded (FIG. 3b). To determine the nucleotide sequence preference of CARD1, CARD1 was incubated with RNA oligos with either 15 adenines, uracils, or cytosines, with a 5' fluorophore and a 3' quencher. CARD1 was able to efficiently degrade RNAs consisting of all three bases, showing broad sequence tolerance for CARD1 (FIG. 3c). We were unable to test guanine because guanines forming G quadruplexes which are resistant to cleavage.

Figure 4:
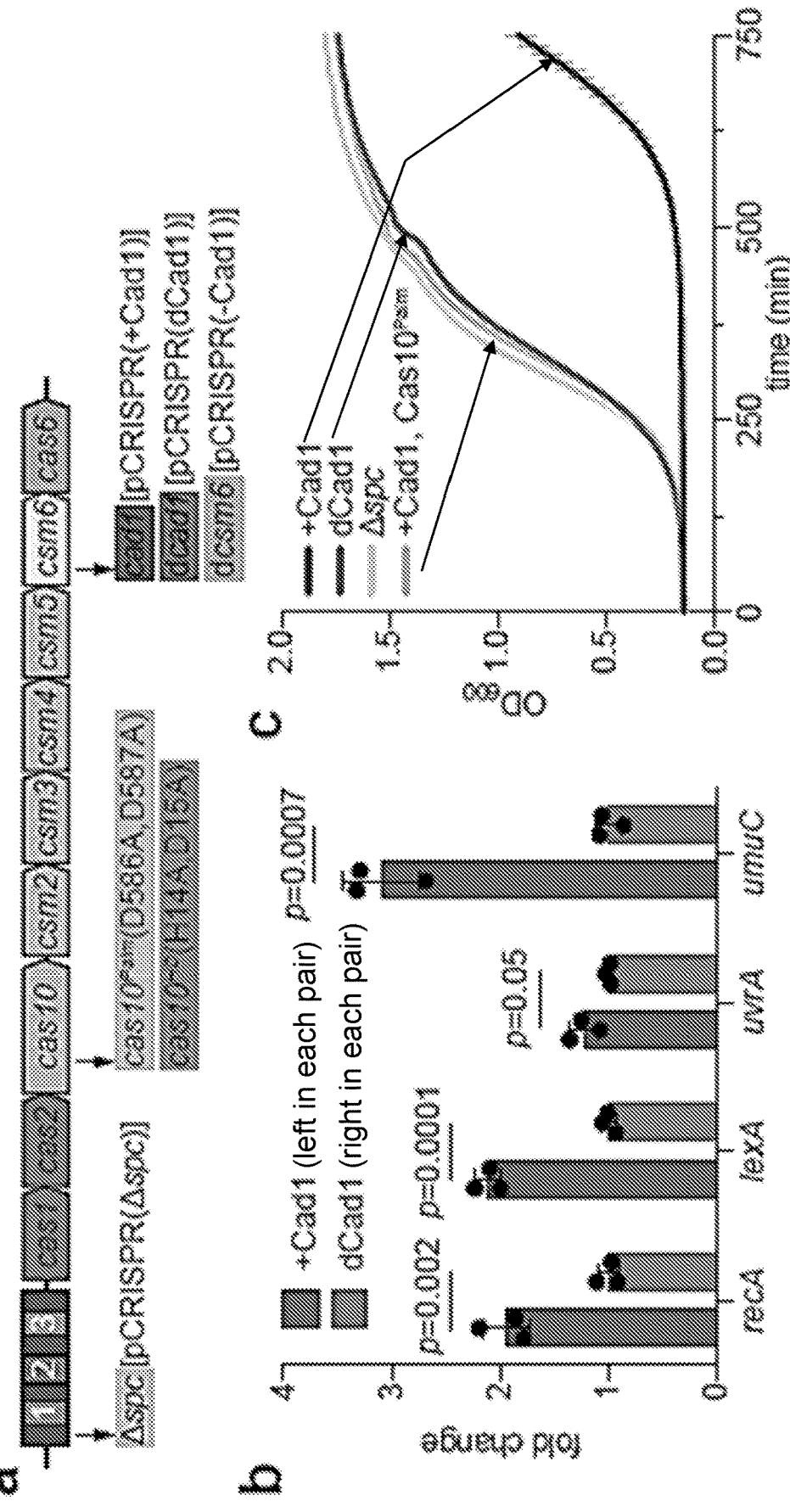
FIG. 4. CARD1 activation leads to a growth arrest of the cell and the destruction of target plasmids. (a) Schematic of the S. epidermidis type III-A locus showing the replacement of csm6 by CARD1 and the different mutations investigated in this study. (b) RT-qPCR of genes whose transcription is activated by the SOS response, using RNA from cells expressing Cas10HD in which CARD1 or dCARD1 was activated by the type III-A immune response against a target plasmid. Mean of three biological replicates ±s.e.m are reported. p values were obtained with two-sided t-test. (c) Growth of staphylococci carrying different pCRISPR variants, measured as OD600 after the addition of aTc to induce the production of cA4 by the Cas10 complex. Mean of three biological triplicates ±s.e.m. are reported. (d) Enumeration of colony-forming units (cfu) from staphylococcal cultures carrying different pCRISPR variants where cA4 production was activated by the addition of aTc. At the indicated times after induction aliquots were removed and plated on solid media with or without aTc to count the remaining viable cells. Mean of three biological replicates ±s.e.m are reported. (e-f) pTarget plasmid curing assay, where plasmid DNA was extracted from cells containing pTarget and different pCRISPR plasmids after induction with aTc. Plasmids were linearized and visualized by gel electrophoresis. Gel images are representative of three independent experiments.
Figure 4:
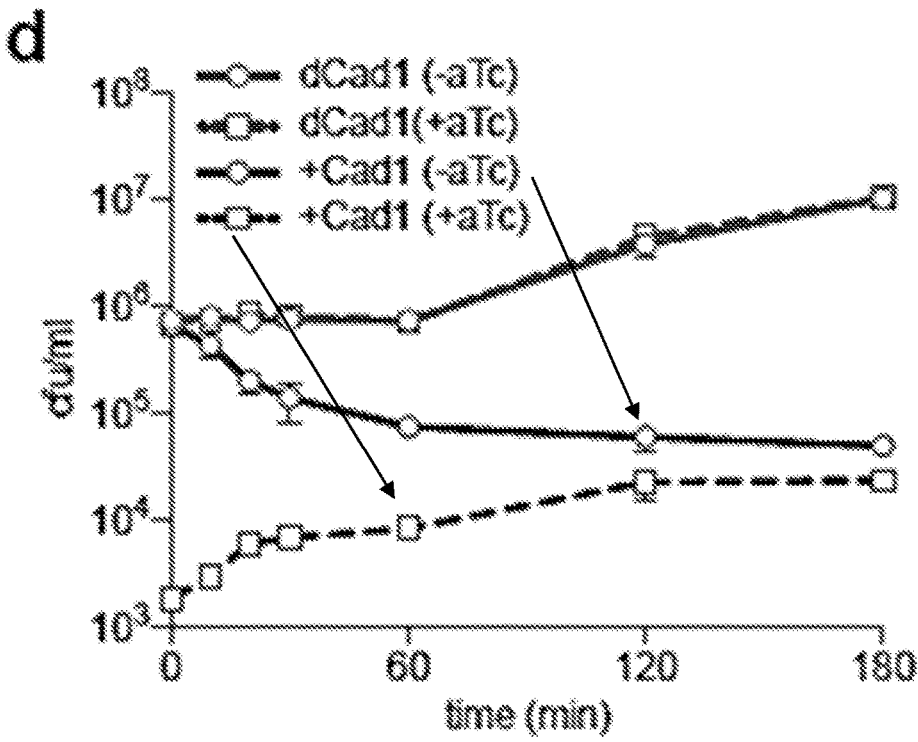
Figure 4:
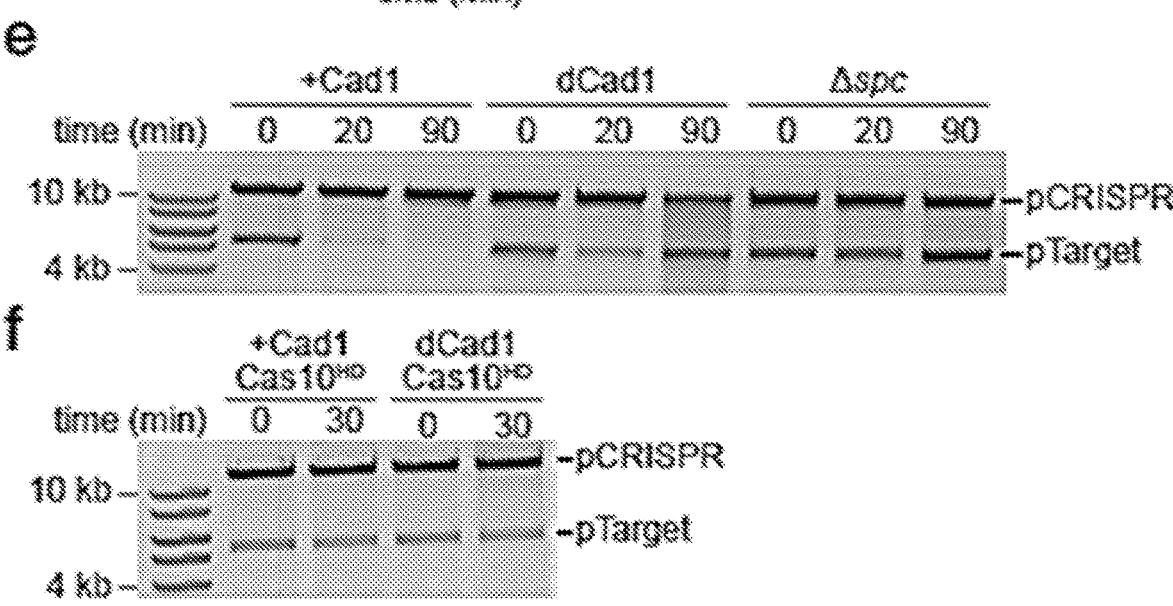
Figure 5:
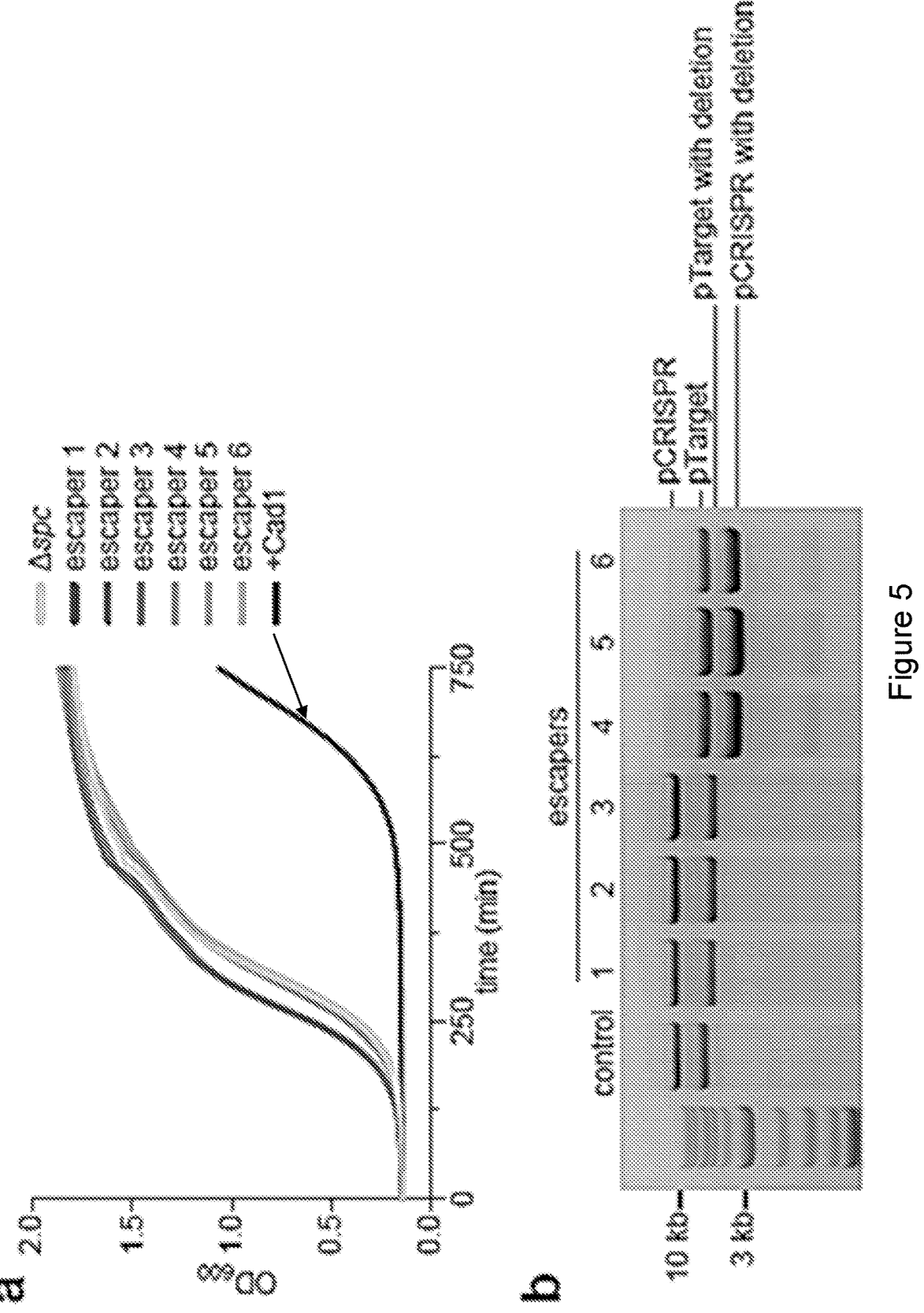
FIG. 5. CARD1-induced cell toxicity. (a) Growth of staphylococci carrying different pCRISPR(+CARD1) taken from six escaper colonies obtained in FIG. 3c, measured as OD600 after the addition of aTc to induce the production of cA4 by the Cas10 complex. Mean of three biological triplicates ±s.e.m. are reported. (b) Agarose gel electrophoresis of plasmid DNA was extracted from escaper cells grown in (a), showing deletions in pTarget or pCRISPR. The deletions were confirmed by Sanger sequencing. (c) Growth of staphylococci carrying different pCRISPR variants expressing Cas10HD, measured as OD600 after the addition of aTc to induce the production of cA4 by the Cas10HD complex. Mean of three biological triplicates ±s.e.m. are reported. (d) Enumeration of colony-forming units (cfu) within staphylococcal cultures carrying different pCRISPR variants expressing Cas10HD where cA4 production was activated by the addition of aTc. At the indicated times after induction aliquots were removed and plated on solid media with or without aTc to count the remaining viable cells. Mean of three biological replicates ±s.e.m are reported. (e) Growth of staphylococci carrying different pCRISPR(+CARD1, Cas10HD) taken from five escaper colonies obtained in (c), measured as OD600 after the addition of aTc to induce the production of cA4 by the Cas10HD complex. Mean of three biological triplicates ±s.e.m. are reported. (f) Agarose gel electrophoresis of plasmid DNA was extracted from escaper cells grown in (e), showing deletions in pTarget. The deletions were confirmed by Sanger sequencing.
Figure 5:
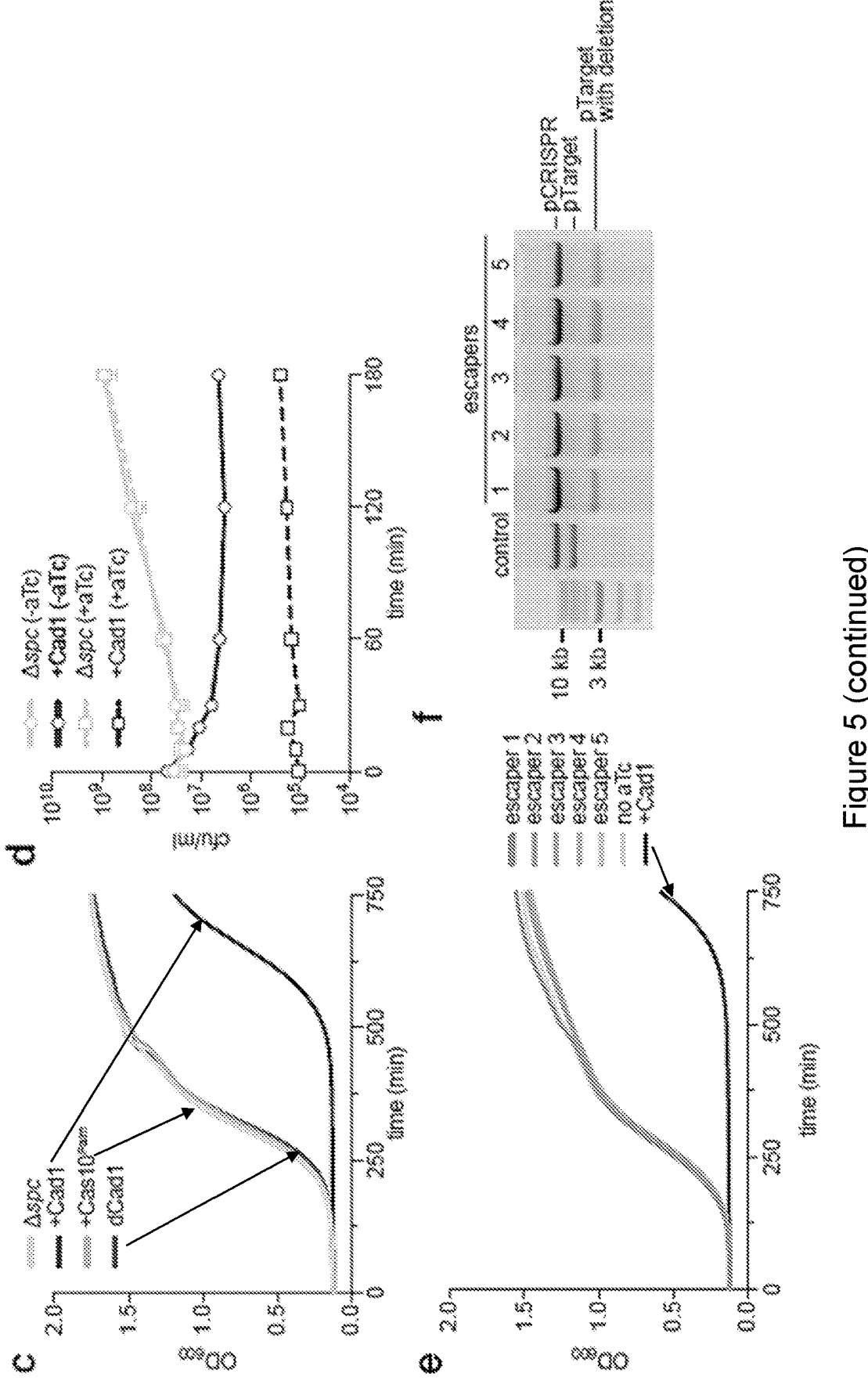

Next, we investigated the function of CARD1 during the type III-A CRISPR-Cas immune response. We determined whether or not the non-specific ssDNA degradation could introduce chromosomal lesions, for example on R-loops generated during transcription or ssDNA intermediates that result from DNA replication. If this is correct, the activation of the type III-A immunity would (i) induce the SOS response to DNA damage (21) and (ii) result in toxicity for the host cell. To test these predictions, we constructed pCRISPR(+CARD1) by cloning into the staphylococcal plasmid pC194 (22) the *Staphylococcus epidermidis* RP62 type III-A locus (2) carrying the CARD1 open reading frame instead of that of the cA-activated accessory protein of this system, Csm6 (FIG. 4a). As a control we introduced mutations that inactivate CARD1 (E308A, K310A) in pCRISPR (dCARD1), that inactivate Csm6 in pCRISPR(−CARD1) or that lack a targeting spacer in pCRISPR(Δspc). Each of these plasmids were transformed into *Staphylococcus aureus* RN4220 (23) cells containing pTarget, a second plasmid producing a target transcript, i.e. complementary to the crRNA expressed by the pCRISPR plasmids, that is under the control of an anhydrotetracycline(aTc)-inducible pro-moter (14). We then added the inducer to trigger the type III-A response and the production of cA by the Palm domain of Cas10 in the different cultures. To examine the SOS response in the presence of activated CARD1, we used RT-qPCR to measure the levels of recA, lexA, uvrA and umuC transcripts (normalized against the rho transcript), which are derepressed by the SOS pathway (24). We observed a significant increase for the expression of all four genes in +CARD1 cultures, compared to d-CARD1 (FIG. 4b). To determine if CARD1 activation is toxic for the host cell, we monitored the growth of the different cultures after the addition of aTc, in the absence of antibiotic selection of pTarget (FIG. 4c). dCARD1 cultures continued exponential growth, similarly to Δspc cells that cannot trigger the type III-A CRISPR-Cas immune response. In contrast, +CARD1 cultures displayed a severe growth defect after the induction of target transcription, which was completely eliminated by the introduction of mutations in the Palm domain of Cas10 (D586A, D587A; Cas10$^{Palm}$) that prevent the production of cA (FIG. 4c). We observed an increase in OD600 at around 10 hours after addition of aTc, which was a result of the propagation of "escaper" cells carrying re-arranged, non-functional pCRISPR or pTarget plasmids within +CARD1 cultures (FIGS. 5a, b). The lack of growth induced by CARD1 could be due to either the arrest or the death of individual cells within the culture. To distinguish between these possibilities, we enumerated viable staphylococci after CARD1 induction, plating culture aliquots taken at different times after addition of aTc on solid media lacking the inducer (FIG. 4d). This procedure removes the inducer and allows the formation of colonies from cells that were arrested in the liquid culture, but not from those that died after activation of CARD1. Over a course of three hours of target transcription and CARD1 activation, we observed that while dCARD1 cultures displayed a steady increase in colony formation, +CARD1 cultures showed an initial decrease in colony counts of an order of magnitude that stabilized after one hour, demonstrating the presence of a population of viable cells that cannot grow, but do not die, upon activation of the nuclease. To determine what fraction of these colonies are escapers, we also enumerated colonies resistant to aTc induction (FIG. 4d) and found that approxi-mately half of the colonies formed in the absence of aTc come from bona fide dormant cells. Finally, we looked at the effects of CARD1 activation on pTarget by agarose gel electrophoresis of plasmid DNA extracted at different time points after aTc addition (FIG. 4e). In dCARD1 cultures the plasmid remained intact for 120 minutes after the activation of cA production, similarly to the Δspc control. In contrast, +CARD1 cells cleared pTarget, but not pCRISPR, 20 min-utes after addition of the inducer. However, in cells lacking the ssDNase activity of Cas10 (H14A, D15A; Cas10$^{HD}$), pTarget remained intact (FIG. 4f) and the growth CARD1-mediated growth arrest was maintained (FIGS. 5c-f), a result that highlights the importance of both Cas10 DNA destruc-tion and CARD1 replication halt for the clearance of the target DNA. Altogether, these results show that CARD1 activation by the type III-A CRISPR-Cas immune response leads to induction of the SOS response and severe toxicity that results in the generation of a population of host cells with arrested growth in which the target DNA is degraded mainly by Cas10.

Figure 6:
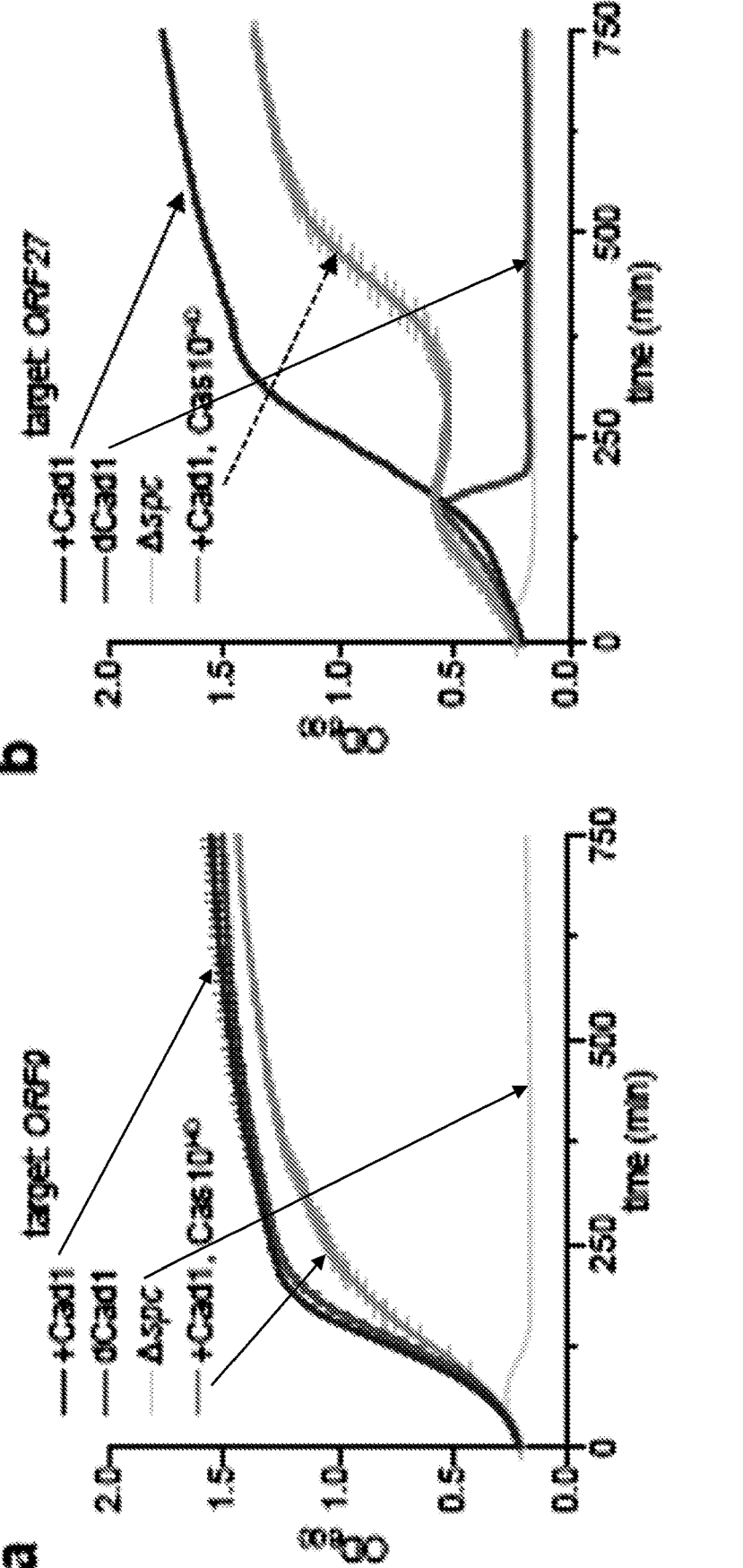
FIG. 6. CARD1 protects staphylococci from phage infection. (a) Growth of staphylococci carrying different pCRISPR variants programmed to target the ORFS transcript of Φ12γ3, measured as OD600 at different times after infection at a multiplicity of infection (MOI) between 2 and 8. Mean of three biological triplicates ±s.e.m. are reported. (b) Same as in (a) but targeting the ORF27 transcript at an MOI ~8. Mean of three biological triplicates f±s.e.m. are reported. (c) Same as in (b) but following cultures carrying different mutations in the cA4 binding pocket of CARD1, at an MOI ~15. (d) Enumeration of plaque-forming units (pfu) within staphylococcal cultures carrying different pCRISPR variants after infection with Φ12γ3. At the indicated times after infection aliquots were removed and plated on top agar media seeded with a susceptible strain. Mean of three biological replicates ±s.e.m are reported.
Figure 6:
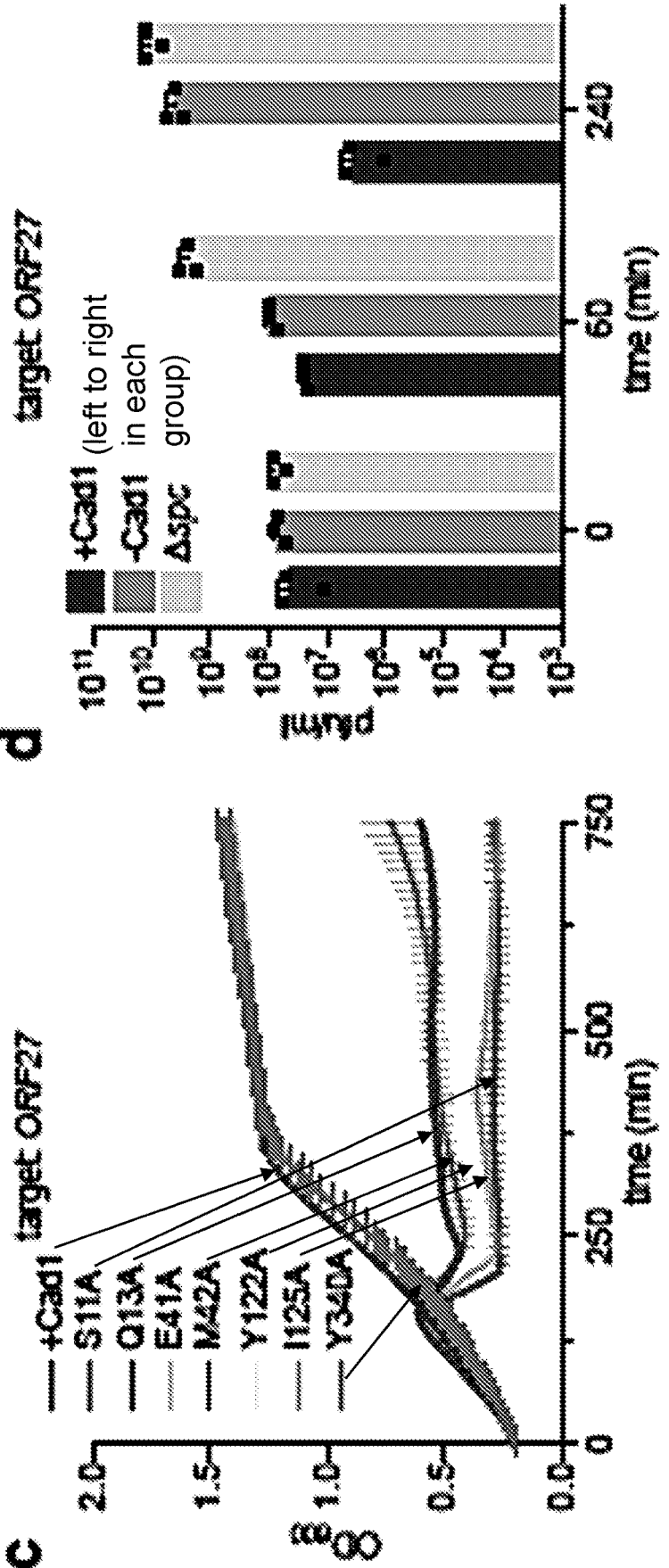
Figure 7:
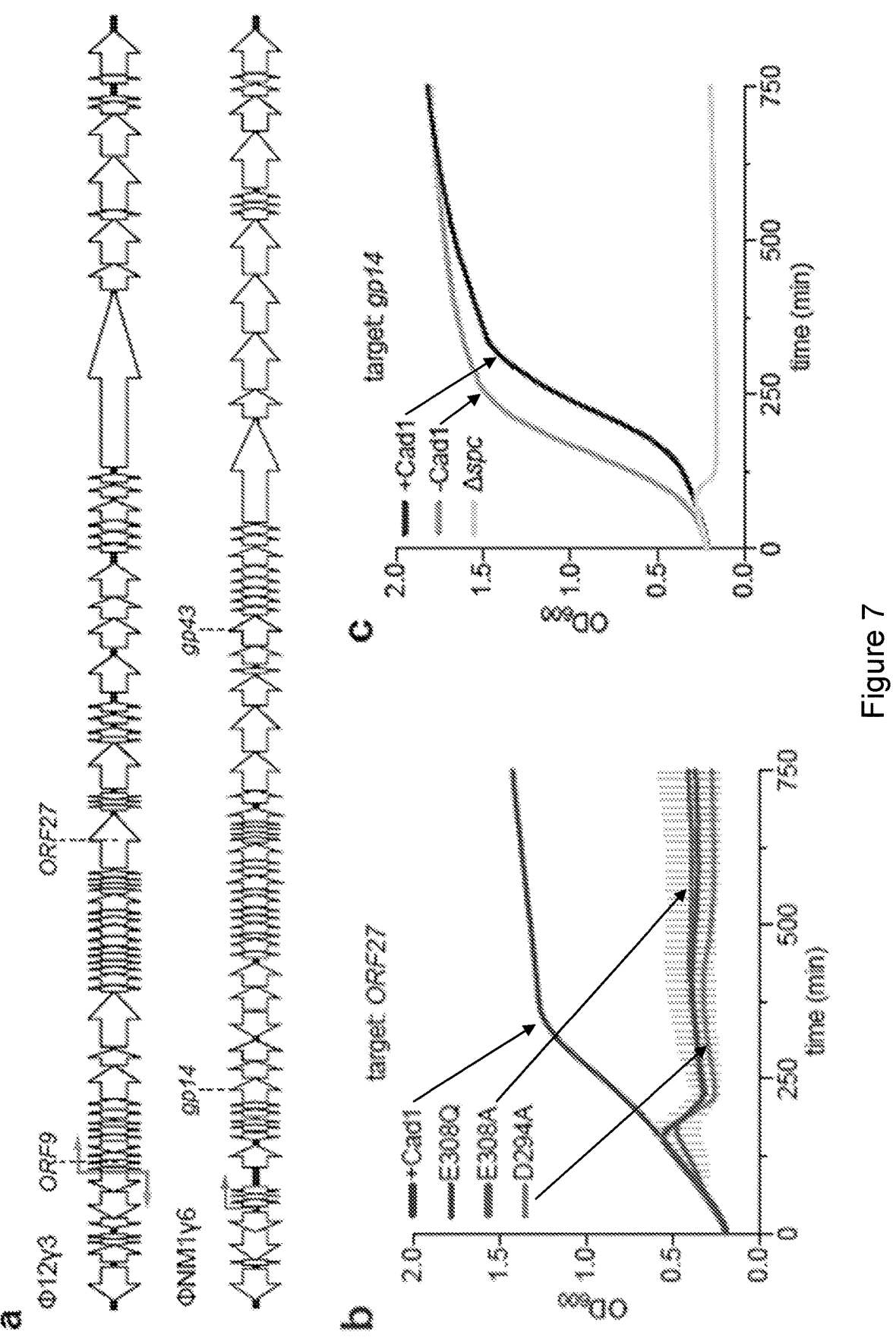
FIG. 7. CARD1-mediated anti-phage immunity. (a) Schematic of the genomes of the staphylococcal phages used in this study, Φ12γ3 and ΦNM1γ6, showing the location of the transcripts targeted by the type III-A CRISPR-Cas system. Grey arrows indicate promoters. (b) Growth of staphylococci carrying different pCRISPR variants with mutations in the catalytic pocket of CARD1, programmed to target the ORF27 transcript of Φ12γ3, measured as OD600 at different times after infection, at an MOI ~15. Mean of three biological triplicates ±s.e.m. are reported. (c) Growth of staphylococci carrying different pCRISPR variants programmed to target the gp14 transcript of ΦNM1γ6, measured as OD600 at different times after infection, at an MOI ~15. Mean of three biological triplicates s.e.m. are reported. (d) Same as in (c) but targeting the gp43 transcript, at an MOI ~2. Mean of three biological triplicates ±s.e.m. are reported.
Figure 7:
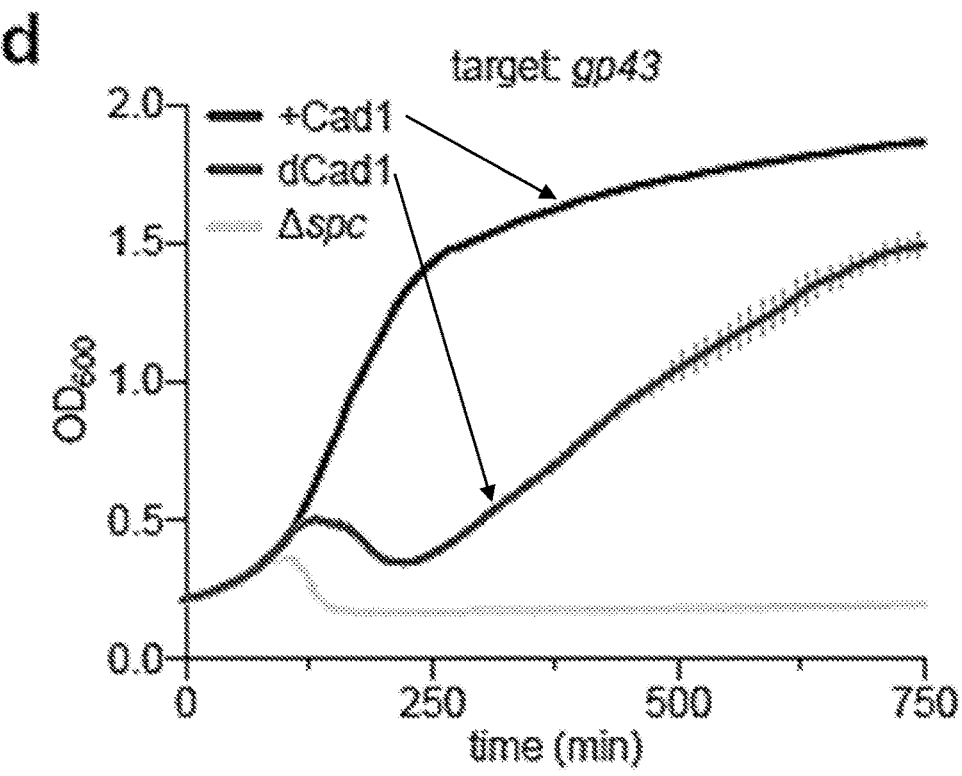
Figure 7:
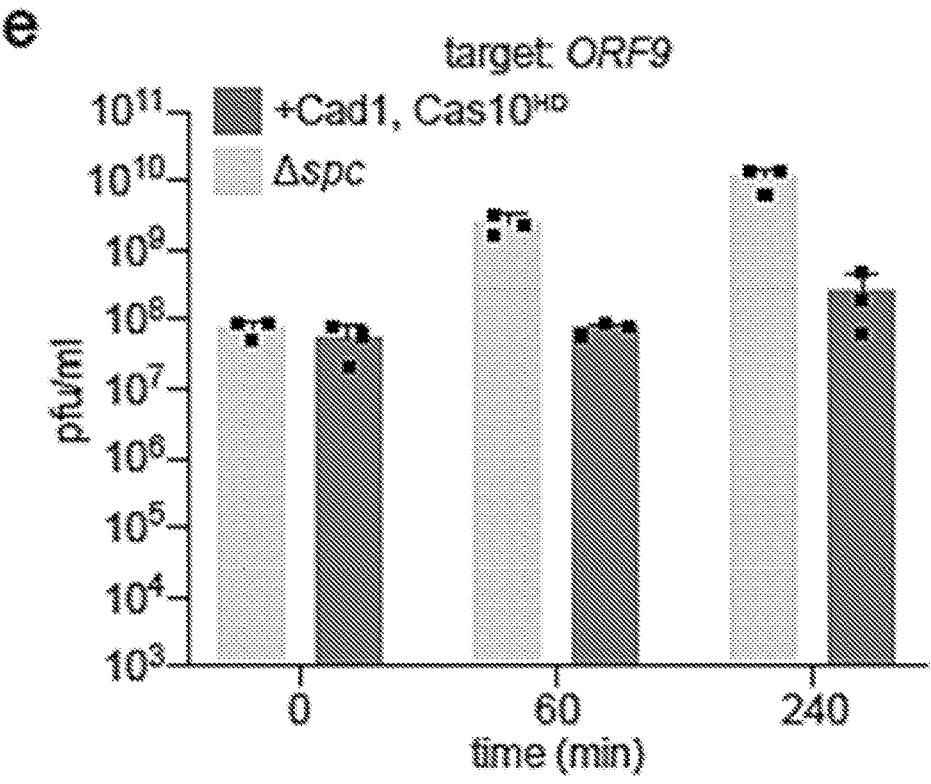

We also tested the importance of CARD1 during immunity against phage infection. Due to the dependence on target transcription to activate the HD domain of Cas10, type III-A immunity results in the rapid elimination of the phage DNA from the host when the target is expressed early during infection and the viral genome has not yet replicated to increase its copy number (15). In contrast, when the viral target is located in a late-expressed transcript, the Cas10 complex can only initiate its attack on the invading DNA after the phage has replicated and accumulated in the host. In this situation the complete degradation of the viral genomes within the infected cells is much slower (15). We programmed the different pCRISPR plasmids with spacers targeting either early- or late-expressed viral genes, infected the cultures with staphylococcal virulent phages and followed their growth to determine the effectiveness of the type III-A immune response in the presence or absence of CARD1. As expected from previous results (15), when the early ORF9 transcript of phage $\Phi12\gamma3$ (25) was targeted, the presence of CARD1 nuclease activity was not required for immunity (FIGS. 6a, 7a). In contrast, when immunity was activated by the late ORF27 transcript, +CARD1 but not dCARD1 cultures were able to survive infection (FIGS. 6b and 6b). Survival also required the ability to bind $cA_4$, as mutations in the nucleotide binding pocket also prevented immunity (FIG. 6c). Similar results were obtained when the pCRISPR plasmids were programmed with spacers that target an early or late transcript of the staphylococcal phage $\Phi NM1\gamma6$ (26) (FIGS. 7a, c-d). We also measured phage propagation in cells programmed to target the ORF27 transcript of $\Phi12\gamma3$ (FIG. 7a), by counting plaque forming units (pfu) at different times after infection (FIG. 6d). We found that while the phage propagated to high titers in both −CARD1 and $\Delta$spc cultures, +CARD1 cells effectively eliminated $\Phi12\gamma3$ from the culture. Finally, we investigated whether CARD1 nuclease activity was sufficient to provide immunity by infecting cells that express Cas10$^{HD}$ in the presence or absence of CARD1. Remarkably, both when the ORF9 (FIG. 6a) and ORF27 (FIG. 6b) transcripts were targeted by the Cas10 complex, CARD1 alone was able to provide immunity to growing cells as well as reduce the phage titer in the cultures (FIG. 7e). Altogether, these results demonstrate that CARD1 nuclease activity is sufficient to provide anti-phage defense in staphylococci and also required for an efficient type III-A CRISPR-Cas immune response when the target is expressed late after infection.

Type III CRISPR-Cas systems employ cA second messengers to activate auxiliary proteins needed for immunity (9, 10). The most common accessory proteins are the non-specific ssRNases Csm6 and Csx1 (16, 17). The present disclosure reveals how the ssDNase and ssRNase CARD1 is activated by $cA_4$ to assist the type III-A CRISPR-Cas response against phages. We found that not only the function of CARD1 but also its activation differs from the previously described RNases. We can also compare CARD1 with Can1, a type III-associated, CARF-containing nickase activated by $cA_4$ (19), and NucC, an effector of the CBASS defense which non-specific dsDNA endonuclease activity is triggered by binding of $cA_3$ (28). While Can1 contains a pair of CARF domains and a single nuclease domain and binds $cA_4$ as a monomer, NucC adopts a trimeric scaffold which binds one molecule of $cA_3$ to promote the formation of a dimer of trimers with endonuclease activity.

In vivo, activation of CARD1 resulted in cell toxicity that produced a growth arrest followed by the death of a substantial fraction of the host population. In addition, both Cas10 and CARD1 ssDNase activities were required for efficient clearance of a target plasmid. During phage infection, CARD1 was necessary for defense when the target transcript recognized by the crRNA in the Cas10 complex is expressed late in the viral lytic cycle, but it was also sufficient to allow survival of a host population lacking the ssDNase activity of Cas10, both when activated by $cA_4$ production early and late during infection. Based on these data we propose that CARD1 protective function is achieved by two separate but overlapping mechanisms. On one hand CARD1 toxicity can provide an abortive infection mechanism of defense in which compromised cells stop growing and prevent the exponential replication of the phage. This activity is similar to the function of Csm6 during type III-A immunity against plasmid-borne, weakly transcribed targets (13, 14) and viral threats recognized late in the infection cycle (15), and it is believed to not only constrain viral propagation and allow the growth of the non-infected cells, but also to facilitate the clearance of the foreign DNA within infected, non-growing cells by Cas10. Interestingly, CARD1 orthologs are present in type III-D systems (18), where Cas10 naturally lacks a functional HD domain and is predicted to be unable to destroy the invader's DNA. Therefore the presently provided results suggest that these systems might protect the host population via a crRNA-guided abortive infection mechanism, similar to the defense provided by type VI systems (29). On the other hand, in contrast to Csm6, CARD1 could directly destroy the phage genome. Many phages and plasmids copy their DNA through rolling-circle replication, which involves the formation of ssDNA intermediates (30), likely making them sensitive to CARD1 digestion. Moreover, since Cas10 also cuts ssDNA, possibly at the transcription fork of the target (8), it could generate more ssDNA intermediates that are sensitive to CARD1 cutting, a hypothesis that explains our result showing synergy between both nucleases to specifically destroy pTarget (FIGS. 4e, f).

The lower prevalence of CARD1 across prokaryotic sequences compared to Csm6/Csx1 (16-18) contrasts with its efficient ability to provide immunity against phage infection. It is possible that the potent toxicity we observed for CARD1 could be detrimental for the host organism if randomly triggered, for example by accidental off-target activation of the Cas10 complex. Due to their sparse appearance in genomic databases, the presence of CARD1 orthologs is limited to organisms that are difficult to culture in laboratory conditions and cannot be genetically manipulated (18). Thus we decided to study CARD1 function as an accessory protein of the type III-A CRISPR-Cas system of *S. epidermidis*, in staphylococci. Because CRISPR-Cas loci are able to transfer horizontally between different species to provide defense without the need of host factors (with only a few exceptions), we believe that our findings for CARD1 would apply to its function in the native host *Treponema succinifaciens*. Supporting this idea, we previously found that the Palm domain of *S. epidermidis* Cas10 produces $cA_6$ to heterologously activate *Enterococcus italicus* Csm6 in staphylococcal hosts (10). Therefore the present results showing that CARD1 is activated by $cA_4$ but not $cA_6$ indicate that the *S. epidermidis* Cas10 complex is able to produce cA rings of different sizes to activate a wide range of CARF-containing proteins, offering the possibility for the functional genetic exchange of type III accessory proteins. Our study highlights the variety of defense systems and mechanisms that prokaryotic organisms have evolved to counteract the diversity and rapid evolution of their genetic parasites.

The following materials and methods were used to describe the foregoing results.

Methods

Protein Expression and Purification

The corresponding sequence of full-length CARD1 (1-372) was cloned to plasmid pJTR330 with a C-terminal hexahistidine (His6)-tag. The protein was overexpressed in E. coli strain BL21-CodonPlus(DE3)-RIL (Stratagene). Bacteria were grown at 37° C. to OD600 of 0.8 and induced by 0.5 mM isopropyl β-D-1-thiogalactopyranoside (IPTG) at 18° C. overnight. Bacteria cells were lysed by sonication in buffer A (20 mM Tris-HCl, 500 mM NaCl, pH 8.0) supplemented with 20 mM imidazole and 1 mM phenylmethylsulfonyl fluoride (PMSF). Cell lysates were centrifuged, and the supernatant was loaded onto a 5 mL HisTrap FF column (GE Healthcare) with extensive washing by buffer A supplemented with 50 mM imidazole. The target protein was eluted with buffer A supplemented with 300 mM imidazole. The eluate was further purified on 5 mL HiTrap Heparin column (GE Healthcare) by a linear gradient from 100 mM to 1 M NaCl, and then on Superdex 200 16/60 column pre-equilibrated in buffer B (20 mM Tris-HCl, pH 7.5, 150 mM NaCl, 1 mM DTT). The high purity eluting fractions were detected by SDS-PAGE and collected. The protein was flash-frozen in liquid nitrogen and stored at –80° C.

In Vitro DNA/RNA Cleavage Assays

The reactions were done in a reaction buffer (20 mM Tris-HCl, pH 7.5, 150 mM NaCl, 1 mM DTT, and 5 mM MnCl$_2$, unless otherwise stated, with 250 nM CARD1 and 2.5 uM of cA4, with 2 μg M13 ssDNA (NEB) (FIG. 1b), 500 ng of non-linearized and linearized ΦX174 dsDNA (NEB) (FIGS. 1d, e, respectively) and 2 μg ΦX174 ssDNA (NEB) (FIG. 1a). cA4 and cA6 was obtained from Biolog Life Science Institute GmbH & Co. KG (Bremen, Germany). The reaction products were visualized by agarose gel electrophoresis. For the RNA oligo cleavage assay, 250 nM of a Cy3-labelled RNA oligo was added to the reaction. The reaction products were run on Mini-PROTEAN TBE-Urea precast gel (Bio-Rad), and visualized on a TYPHOON IMAGE SCANNER. For degradation of ssRNA or dsRNA ladders, 1 ug of either ssRNA ladder (NEB) or dsRNA ladder (NEB) was digested. The reaction products were visualized by agarose gel electrophoresis. At the indicated timepoints, all reaction were stopped by the addition of 25 mM of EDTA.

For determining the nucleotide cleavage preference of CARD1, the reaction was performed as above, with 1 uM of each RNA oligo (IDT). The RNA oligos had a 5' end fluorophore (FAM) and a 3' end quencher (Iowa black), generating a fluorescent signal upon cleavage of the linker RNA. Fluorescent measurements were taken in a TECAN plate reader, using values from when the reaction was complete. 0.5 ul of RNaseI (Thermo Fisher Scientific), which cuts next to all RNA nucleotides, was used as a positive control.

Bacterial Growth

S. aureus strain RN4220 (23) was grown in brain heart infusion (BHI) medium at 37° C., supplemented with chloramphenicol at 10 μg/ml for maintaining pCRISPRs, and erythromycin at 10 μg/ml for maintaining pTarget. 5 μM CaCl$_2$ was supplemented in phage experiments.

Molecular Cloning

The Plasmids Used in this Study are Listed in the Tables. The Oligonucleotides used for this cloning are listed in the tables. The cloning strategies for generating these plasmids are listed in the tables. For obtaining the coding sequence of CARD1, the amino acid sequence of Tresu_2185 (NCBI Reference Sequence WP_013702306.1) from Treponema succinifaciens DSM 2489 was codon optimized for expression in S. aureus and synthesized by Genewiz (NJ, USA). In embodiments, the disclosure thus comprises a codon optimized cDNA, and expression vectors comprising the cDNA sequence.

Growth Curves

For in vivo CARD1 toxicity induction, triplicate RN4220 overnight cultures harbouring pTarget and a pCRISPR are diluted 1:100, outgrown for about an hour, and normalized for OD. Cells are then seeded in a 96 well plate. To induce targeting, 6.25-12.5 ng/ml of anhydrotetracycline (aTc) is added to the appropriate wells. Absorbance at 600 nm is then measured every 10 minutes by a microplate reader (TECAN Infinite 200 PRO). To analyze targeting escapers, cells from the end of the experiment (either cells from wells without aTc, i.e. naïve cells, or cells from wells that recovered later in the time course due to CARD1 toxicity) are re-streaked on BHI agar plates, and individual colonies were launched in liquid culture, diluted the next day, and used for a new time course experiment. From these overnight cultures, plasmid DNA was isolated (QIAgen Spin Miniprep Kit), digested by BamHI-HF (single-cutter for both pTarget and pCRISPR) (New England Biolabs), and visualized by gel electrophoresis. The deletion of important features in pTarget (making it unable to be targeted by pCRISPR) or pCRISPR was confirmed by Sanger sequencing.

For in vivo anti-phage immunity, cells harbouring various pCRISPRs were launched in triplicate overnight, diluted 1:100, outgrown for about an hour, and normalized for OD. Cells were seeded into a 96 well plate. Phage Φ12γ3 (25) ΦNM1γ6 (26) or was added at the appropriate multiplicity of infection, and OD measurements were taken every 10 minutes.

CARD1 Toxicity Assay

To measure the effect of CARD1 activity on S. aureus viability over time, colonies of S. aureus harbouring pTarget and the specified pCRISPR were launched in liquid culture overnight in triplicate. The next day, cells were diluted 1:100 and grown out for about an hour, and normalized for OD. One aliquot was taken from each culture, and then aTc was added to induce CRISPR targeting and CARD1 activity (to a concentration of 3 ng/ml in FIG. 4c or 125 ng/ml in FIG. 5c). At each timepoint, cell aliquots were removed, centrifuged, resuspended in media lacking aTc, and serial dilutions were plated on solid BHI agar plates with or without aTc. All viable cells should grow on the solid agar plates, but only targeting escapers (cells that recover due to mutations in pTarget or pCRISPR) should form CFUs on plates with aTc.

Liquid Anti-Phage Infection

To obtain CFU and PFU counts over time from cultures infected with phage, RN4220 cultures harbouring various pCRISPRs were launched overnight, diluted 1:100, and outgrown for about one hour. Cells were then infected with phage Φ12γ3 at an MOI of 10, and an aliquot was taken shortly after to obtain PFUs at time 0. The cultures were then incubated further, with aliquots taken at 1 and 4 hours.

Plasmid Curing

To assess CARD1's ability to promote plasmid curing under low transcription conditions, a plasmid curing assay was performed, by adapting a known approach. Briefly, overnight cultures of *S. aureus* cells harbouring pTarget and a pCRISPR containing either Csm6, dCsm6, or CARD1 were diluted to exactly OD 0.15 in tryptic soy broth with 10 ug/ml chloramphenicol. After removing a cell aliquot for the 0 timepoint, aTc was added to a concentration of 9.3 ng/ml (FIG. 4*e*) or 125 ng/ml (FIG. 4*f*) and the cells were incubated at 37° C., with further aliquots taken at the indicated times. The cells were then lysed, and the plasmid DNA isolated using a QIAprep Miniprep kit (Qiagen) according to the manufacturer's protocol (Qiagen). 400 ng of plasmid was then linearized using BamHI-HF (New England Biolabs), which cuts both pTarget and pCRISPR once, followed by visualization by gel electrophoresis.

RT-qPCR of SOS-Induced Genes

Cells carrying pTarget and a pCRISPR containing either CARD1 or dCARD1 were grown overnight in triplicate, diluted 1/100 into fresh BHI with 10 ug/ml of chloramphenicol and outgrown for an hour. The cells were then diluted to an OD of 0.1. To induce targeting, aTc was added to a final concentration of 250 ng/ml. The cells were incubated with shaking for 20 minutes before being spun down at 6000×g for 5 minutes, and then lysed in PBS with 1 mg/ml of lysostaphin and 2 mg/ml of lysozyme for 10 minutes at 37° C. RNA was purified using Direct-zol RNA miniprep kit (Zymo Research) according to the manufacturer's protocol, followed by DNA depletion using TURBO DNA-free kit (Invitrogen) according to the manufacturer's protocol. To produce cDNA, approximately 2 ug of DNA-depleted RNA was treated using the SuperScript IV Reverse Transcriptase kit (Invitrogen) according to the manufacturer's protocol and random hexamer primers. The RT-qPCR reaction was performed using Fast SYBR Green Master Mix (Life Technologies) with an input of about 100 ng cDNA, in biological triplicate, using 0.375 mM of each primer, on a QuantStudio 3 qPCR machine (Thermo Fisher). The housekeeping gene rho was used as an internal normalization control (37).

Next-Generation Sequencing of ssDNA Degradation Products

To assess the ssDNA cleavage patterns of CARD1, 2 ug of ΦX174 virion DNA (New England Biolabs) or M13 ssDNA (M13mp18) (New England Biolabs) was first digested by 250 nM CARD1 with 2.5 uM of cA$_4$ in a buffer consisting of 20 mM Tris pH 7.5, 150 mM NaCl, 1 mM DTT, and 5 mM MnCl$_2$. At the specified time points, the reaction was quenched by adding 25 mM of EDTA. Half the reaction was visualized by agarose gel electrophoresis. The remaining digestion products from the 2 hour timepoint were purified by phenol chloroform extraction.

Without further fragmentation, the purified digested DNA was subjected to the Accel-NGS 1S Plus DNA Library Kit (Swift Biosciences), proceeding according to the manufacturer's protocol, using a 1.5× ratio of magnetic beads (AM-Pure XP beads by Beckman Coulter) to also include small DNA fragments. One of the library preparation steps involves the addition of on average 8 nucleotides to the 3' end of the DNA. The 5' end of the input DNA molecules remains unchanged. Paired-end sequencing was performed on an Illumina MiSeq. The 5' end of each read R1 represents the start of a DNA molecule, and thus a CARD1 cut site. Using a custom python script, the location of 7,020,067 ΦX174 reads (mapping to Genbank reference NC_001422) and 7,670,616 M13 reads (mapping to Genbank reference X02513) was determined. To account for reads mapping at the circular junctions, 65 nucleotides of the first 5' end of the maps were copied and added at the 3' end of the maps. The DNA sequence 20 nucleotides upstream and downstream of the cut sites was extracted using a custom Python script, and the CARD1 cleavage motifs for ΦX174 and the M13 were determined separately using Weblogo3 (38), with basal nucleotide compositions determined by the compositions in each map (ΦX174 with A:24.0, C:21.4, G:23.3, T:31.3, and M13 with A:24.4, C:21.1, G:21.1, T:33.4). For the fragment size analysis, 8 nucleotides were removed from all the reads from the 3' end pair mate by the "Trim Ends" option in the Geneious Bioinformatics Software platform (39). Using the STAR aligner (version 2.7.3) (40), 7,505,136 reads were successfully mapped to ΦX174, and 8,179,356 reads were successfully mapped to M13, using default arguments with the addition of --alignIntronMax 1 --alignMatesGapMax 6000 --peOverlapNbasesMin 5 --alignEndsProtrude 10 ConcordantPair.

TABLE 1

| Plasmids used in this study | | |
| --- | --- | --- |
| Plasmid name | Plasmid contents | Made in this study? |
| pGG-BsaI-R | Type III with no spacer | No (26) |
| pJTR170 | Type III, Φ12γ3 ORF27 spacer, Csm6 | Yes |
| pJTR172 | Type III, Φ12γ3 ORF27 spacer, dCsm6 | Yes |
| pJTR330 | CARD1-His$_6$ on pET23 overexpression | Yes |
| pJTR378 | dCARD1-His$_6$ on pET23 overexpression | Yes |
| pJTR393 | Type III, no targeting spacer, CARD1 | Yes |
| pJTR394 | Type III, anti-pTarget spacer, Cas10$^{HD}$, Cas10$^{Palm}$, CARD1 | Yes |
| pJTR395 | Type III, anti-pTarget spacer, CARD1 | Yes |
| pJTR396 | Type III, anti-pTarget spacer, Cas10$^{HD}$, CARD1 | Yes |
| pJTR400 | Type III, Φ12γ3 ORF9 spacer, CARD1 | Yes |
| pJTR401 | Type III, Φ12γ3 ORF9 spacer, Cas10$^{HD}$, CARD1 | Yes |
| pJTR402 | Type III, Φ12γ3 ORF27 spacer, CARD1 | Yes |
| pJTR403 | Type III, Φ12γ3 ORF27 spacer, Cas10$^{HD}$, CARD1 | Yes |
| pJTR405 | Type III, anti-pTarget spacer, CARD1 | Yes |
| pJTR406 | Type III, anti-pTarget spacer, Cas10$^{HD}$, dCARD1 | Yes |
| pJTR424 | Type III, Φ12γ3 ORF27 spacer, CARD1$^{Q13A}$ | Yes |
| pJTR426 | Type III, Φ12γ3 ORF27 spacer, CARD1$^{E41A}$ | Yes |
| pJTR427 | Type III, Φ12γ3 ORF27 spacer, CARD1$^{M42A}$ | Yes |
| pJTR428 | Type III, Φ12γ3 ORF27 spacer, CARD1$^{I125A}$ | Yes |
| pJTR429 | Type III, Φ12γ3 ORF27 spacer, CARD1$^{Y340A}$ | Yes |
| pJTR431 | Type III, Φ12γ3 ORF27 spacer, CARD1$^{E308Q}$ | Yes |
| pJTR434 | Type III, Φ12γ3 ORF27 spacer, CARD1$^{S11A}$ | Yes |
| pJTR435 | Type III, Φ12γ3 ORF27 spacer, CARD1$^{E308A}$ | Yes |

TABLE 1-continued

| Plasmids used in this study | | |
|---|---|---|
| Plasmid name | Plasmid contents | Made in this study? |
| pJTR436 | Type III, Φ12γ3 ORF27 spacer, CARD1$^{Y122}$ | Yes |
| pJTR437 | Type III, Φ12γ3 ORF27 spacer, CARD1$^{D294A}$ | Yes |
| pJTR439 | Type III, Φ12γ3 ORF9 spacer, dCARD1 | Yes |
| pJTR441 | Type III, Φ12γ3 ORF27 spacer, dCARD1 | Yes |
| pJTR443 | Type III, ΦNM1γ6 gp14 spacer, CARD1 | Yes |
| pJTR444 | Type III, anti-pTarget spacer, dCARD1 | Yes |
| pJTR446 | Type III, anti-pTarget spacer, Cas10$^{Palm}$, dCARD1 | Yes |
| pTarget | aTc-inducible promoter in front of a protospacer | No |
| pWJ246 | Type III, ΦNM1γ6 gp14 spacer, dCsm6 (-CARD1) | No |

TABLE 2

| Oligonucleotides used in this study | | | |
|---|---|---|---|
| Name | Sequence | Purpose | SEQ ID NO: |
| GG424 | CATATTGCCTGATGAAGTGAATAG | Cloning | 6 |
| GG425 | CTATTCACTTCATCAGGCAATATG | Cloning | 7 |
| JTR476 | GAACAGTGTCTAACAACTGCAATTCACTAAAT GCTGTAA | Cloning | 8 |
| JTR477 | GATCTTACAGCATTTAGTGAATTGCAGTTGTTA GACACT | Cloning | 9 |
| JTR632 | ATGATAAATAAAATTACAGTAGAGTTAGACTT GC | Cloning | 10 |
| JTR633 | TATAGCACCTCATTATTTAACTCTTGAAAAC | Cloning | |
| JTR638 | CAAGAGTTAAATAATGAGGTGCTATAATGAAA GAGACTATTTTGGTTAACTTGG | Cloning | 12 |
| JTR639 | CTAACTCTACTGTAATTTTATTTATCATATGTA TATCTCCTTCTCATAATTGTGTACCGTCTTTAAT GTC | Cloning | 13 |
| JTR678 | GTTACACGTGATAGCATGTGCTAGTTTCGTCGA TGGAAACG | Cloning | 14 |
| JTR679 | GACGAAACTAGCACATGCTATCACGTGTAACT TATTGTCTTTGTC | Cloning | 15 |
| JTR859 | GATCCGGCTGCTAACAAAGC | Cloning | 16 |
| JTR860 | ATGTATATCTCCTTCTTAAAGTTAAACAAAATT ATTTCTAG | Cloning | 17 |
| JTR861 | GTTTAACTTTAAGAAGGAGATATACATATGAA AGAGACTATTTTGGTTAACTTGG | Cloning | 18 |
| JTR862 | CGGGCTTTGTTAGCAGCCGGATCTTAGTGATG GTGATGGTGATGTCCTG | Cloning | 19 |
| JTR951 | CAACAAAAGTATTTAAACTTTCTTTTAAGACTC | Cloning | 20 |
| JTR952 | GAAAGTTTAAATACTTTTGTTGCCAATGTCATT CACCTACTTAATTTTAAGATTTG | Cloning | 21 |
| JTR972 | AACAATTCCTAATGTACAATTTATCAAGTGG | Cloning | 22 |
| JTR973 | GATAAATTGTACATTAGGAATTGTTGCCTCACT AACCAAGTTAACCAAAATAGTC | Cloning | 23 |
| JTR974 | GAGCAAACAATTCCTAATGTACAATTTATC | Cloning | 24 |
| JTR975 | GTACATTAGGAATTGTTTGCTCTGCAACCAAGT TAACCAAAATAGTCTCTTTC | Cloning | 25 |
| JTR976 | ATGGAACAGAAAGAAAAATCATTGTTC | Cloning | 26 |

TABLE 2-continued

Oligonucleotides used in this study

| Name | Sequence | Purpose | SEQ ID NO: |
|---|---|---|---|
| JTR977 | CAATGATTTTTCTTTCTGTTCCATTGCCTTAGTA CTCACTAACAATATCTTCATTGG | Cloning | 27 |
| JTR978 | GAACAGAAAGAAAAATCATTGTTCATCAAG | Cloning | 28 |
| JTR979 | GAACAATGATTTTTCTTTCTGTTCTGCCTCCTTA GTACTCACTAACAATATCTTCATTGG | Cloning | 29 |
| JTR980 | AGGTAAAGAATTGCAGGAGTTATACC | Cloning | 30 |
| JTR981 | GTATAACTCCTGCAATTCTTTACCTGCAGGTTG GTAGAATATCTCTGTGTTAGG | Cloning | 31 |
| JTR982 | GTAAAGCAACACTTGTATACGAAAAG | Cloning | 32 |
| JTR983 | CTTTTCGTATACAAGTGTTGCTTTACTGCTAAT CCGAACTTACTCTTGATGATCG | Cloning | 33 |
| JTR984 | ATGTAAGAGTTTCGTCGATGGAAACG | Cloning | 34 |
| JTR985 | CCATCGACGAAACTCTTACATGCTATCACGTGT AACTTATTGTCTTTGTCC | Cloning | 35 |
| JTR986 | AATGTAAGAGTTTCGTCGATGG | Cloning | 36 |
| JTR987 | CCATCGACGAAACTCTTACATTGTATCACGTGT AACTTATTGTCTTTGTCC | Cloning | 37 |
| JTR993 | CAACCTATAGGTAAAGAATTGCAGG | Cloning | 38 |
| JTR994 | CAATTCTTTACCTATAGGTTGTGCGAATATCTC TGTGTTAGGTTTGTTATTAAAGAAATC | Cloning | 39 |
| JTR995 | GTTATCTACTTGGACAAAGACAATAAGTTAC | Cloning | 40 |
| JTR996 | GTCTTTGTCCAAGTAGATAACTGCCAACTCGTT TTTGTCATTTCCC | Cloning | 41 |
| JTR1000 | GTTCAGTTACATTAGATAATGCGCTAGGTG | qPCR primer for recA, F | 42 |
| JTR1001 | CGATAAATGCTGCCACCCCG | qPCR primer for recA, R | 43 |
| JTR1002 | CTGTGACTTTACCAATAACTGGCACATG | qPCR primer for lexA, F | 44 |
| JTR1003 | CTGTTCATGGTCACCTTTCACGTCTTG | qPCR primer for lexA, R | 45 |
| JTR1004 | CGATACTATATATGCTGAAGGACAACGACG | qPCR primer for uvrA, F | 46 |
| JTR1005 | CTTGTTGTTTTTTGATCTATTGAAATTGCTGGC | qPCR primer for uvrA, R | 47 |
| JTR1008 | CGAGTGTTTCTTGTATTGAAAAGGGGC | qPCR primer for umuC, F | 48 |
| JTR1009 | GTGGTATTTCAAACAATCGCGACCC | qPCR primer for umuC, R | 49 |
| W614 | GGTTATACTAAAAGTCGTTTGTTGG | Cloning | 50 |
| W852 | CCAACAAACGACTTTTAGTATAACC | Cloning | 51 |
| W915 | GTCAATGACCATAACGCAGAAG | qPCR primer for rho, F | 52 |
| W916 | CAATCGGTGTTACTAAATCCATG | qPCR primer for rho, R | 53 |

TABLE 2-continued

| | Oligonucleotides used in this study | | |
|---|---|---|---|
| Name | Sequence | Purpose | SEQ ID NO: |
| W1169 | CCGATTAAAAATAAAGCTGCACCGCCTGAATA TATAGCAGTAATTTG | Cloning | 54 |
| W1170 | TATTCAGGCGGTGCAGCTTTATTTTTAATCGGT GCATGGGATG | Cloning | 55 |

TABLE 3

| | Cloning strategy for plasmids used in this study |
|---|---|
| Name | Cloning strategy |
| pJTR170 | Cleavage of plasmid pGG-BsaI-R with BsaI-HF, then ligation of the linearized plasmid with the annealed oligo pair JTR476 and JTR477 |
| pJTR172 | PCR amplification of pJTR170 with W852 and GG425, and of pWJ241 with GG424 and W614, followed by Gibson assembly of the two PCR products |
| pJTR330 | PCR amplification of pPS3 with JTR859 and JTR860, and with pJTR325 by JTR861 and JTR862, followed by Gibson assembly of the two PCR products |
| pJTR378 | PCR amplification of pJTR330 by JTR861 and JTR679, and with JTR860 and JTR678 |
| pJTR393 | PCR amplification of pGG-BsaI-R with W852 and GG425, and of pRF7 with GG424 and W614, followed by Gibson assembly of the two PCR products |
| pJTR394 | PCR amplification of pJTR121 with W852 and GG425, and of pRF7 with GG424 and W614, followed by Gibson assembly of the two PCR products |
| pJTR395 | PCR amplification of pWJ191 by JTR633 and JTR632, and of pJTR224 by JTR638 and JTR639, followed by Gibson assembly of the two PCR products |
| pJTR396 | PCR amplification of pJTR125 with JTR632 and JTR633, and of pJTR224 with JTR638 and JTR639, followed by Gibson assembly of the two PCR products |
| pJTR400 | PCR amplification of pJTR169 with W852 and GG424, and of pJTR395 with W614 and GG424, followed by Gibson assembly of the two PCR products |
| pJTR401 | PCR amplification of pJTR169 with W852 and GG424, and of pJTR396 with W614 and GG424, followed by Gibson assembly of the two PCR products |
| pJTR402 | PCR amplification of pJTR170 with W852 and GG425, and of pJTR395 with GG424 and W614, followed by Gibson assembly of the two PCR products |
| pJTR403 | PCR amplification of pJTR170 with W852 and GG425, and of pJTR396 with GG424 and W614, followed by Gibson assembly of the two PCR products |
| pJTR405 | PCR amplification of pJTR395 with JTR678 and W614, and with JTR679 and W852, followed by Gibson assembly of the two PCR products |
| pJTR406 | PCR amplification of pJTR396 with JTR678 and W614, and with JTR679 and W852, followed by Gibson assembly of the two PCR products |
| pJTR424 | PCR amplification of pJTR402 with JTR972 and W614, and with JTR973 and W852, followed by Gibson assembly of the two PCR products |
| pJTR426 | PCR amplification of pJTR402 with JTR976 and W614, and with JTR977 and W852, followed by Gibson assembly of the two PCR products |
| pJTR427 | PCR amplification of pJTR402 with JTR978 and W614, and with JTR979 and W852, followed by Gibson assembly of the two PCR products |
| pJTR428 | PCR amplification of pJTR402 with JTR980 and W614, and with JTR981 and W852, followed by Gibson assembly of the two PCR products |
| pJTR429 | PCR amplification of pJTR402 with JTR982 and W614, and with JTR983 and W852, followed by Gibson assembly of the two PCR products |
| pJTR431 | PCR amplification of pJTR402 with JTR986 and W614, and with JTR987 and W852, followed by Gibson assembly of the two PCR products |
| pJTR434 | PCR amplification of pJTR402 with JTR974 and W614, and with JTR975 and W852, followed by Gibson assembly of the two PCR products |
| pJTR435 | PCR amplification of pJTR402 with JTR984 and W614, and with JTR985 and W852, followed by Gibson assembly of the two PCR products |
| pJTR436 | PCR amplification of pJTR402 with JTR993 and W614, and with JTR994 and W852, followed by Gibson assembly of the two PCR products |
| pJTR437 | PCR amplification of pJTR402 with JTR995 and W614, and with JTR996 and W852, followed by Gibson assembly of the two PCR products |
| pJTR439 | PCR amplification of pJTR400 with W852 and JTR679, and with W614 and JTR678, followed by Gibson assembly of the two PCR products |
| pJTR441 | PCR amplification of pJTR402 with W852 and JTR679, and with W614 and JTR678, followed by Gibson assembly of the two PCR products |
| pJTR443 | PCR amplification of pJTR288 with W852 and JTR952, and with W614 and JTR951, followed by Gibson assembly of the two PCR products |
| pJTR444 | PCR amplification of pJTR109 with W852 and GG425, and of pJTR441 with W614 and GG424, followed by Gibson assembly of the two PCR products |
| pJTR446 | PCR amplification of pJTR395 with W852 and W1169, and with W614 and W1170, followed by Gibson assembly of the two PCR products |

References—this reference listing is not an indication that any reference(s) are material to patentability.

1. R. Barrangou et al., CRISPR provides acquired resistance against viruses in prokaryotes. Science 315, 1709-1712 (2007).
2. L. A. Marraffini, E. J. Sontheimer, CRISPR interference limits horizontal gene transfer in staphylococci by targeting DNA. Science 322, 1843-1845 (2008).
3. S. J. Brouns et al., Small CRISPR RNAs guide antiviral defense in prokaryotes. Science 321, 960-964 (2008).
4. R. N. Jackson, P. B. van Erp, S. H. Sternberg, B. Wiedenheft, Conformational regulation of CRISPR-associated nucleases. Curr. Opin. Microbiol. 37, 110-119 (2017).
5. K. S. Makarova et al., Evolutionary classification of CRISPR-Cas systems: a burst of class 2 and derived variants. Nat. Rev. Microbiol. 18, 67-83 (2020).
6. C. R. Hale et al., RNA-guided RNA cleavage by a CRISPR RNA-Cas protein complex. Cell 139, 945-956 (2009).
7. M. Kazlauskiene, G. Tamulaitis, G. Kostiuk, C. Venclovas, V. Siksnys, Spatiotemporal Control of Type III-A CRISPR-Cas Immunity: Coupling DNA Degradation with the Target RNA Recognition. Mol. Cell 62, 295-306 (2016).
8. P. Samai et al., Co-transcriptional DNA and RNA Cleavage during Type III CRISPR-Cas Immunity. Cell 161, 1164-1174 (2015).
9. M. Kazlauskiene, G. Kostiuk, C. Venclovas, G. Tamulaitis, V. Siksnys, A cyclic oligonucleotide signaling pathway in type III CRISPR-Cas systems. Science 357, 605-609 (2017).
10. O. Niewoehner et al., Type III CRISPR-Cas systems produce cyclic oligoadenylate second messengers. Nature 548, 543-548 (2017).
11. N. Jia, R. Jones, G. Yang, O. Ouerfelli, D. J. Patel, CRISPR-Cas III-A Csm6 CARF Domain Is a Ring Nuclease Triggering Stepwise cA4 Cleavage with ApA>p Formation Terminating RNase Activity. Mol. Cell, (2019).
12. R. Molina et al., Structure of Csx1-cOA4 complex reveals the basis of RNA decay in Type III-B CRISPR-Cas. Nat Commun 10, 4302 (2019).
13. K. Foster, J. Kalter, W. Woodside, R. M. Terns, M. P. Terns, The ribonuclease activity of Csm6 is required for anti-plasmid immunity by Type III-A CRISPR-Cas systems. RNA Biol, (2018).
14. J. T. Rostol, L. A. Marraffini, Non-specific degradation of transcripts promotes plasmid clearance during type III-A CRISPR-Cas immunity. Nat Microbiol 4, 656-662 (2019).
15. W. Jiang, P. Samai, L. A. Marraffini, Degradation of phage transcripts by CRISPR-associated RNases enables type III CRISPR-Cas immunity. Cell 164, 710-721 (2016).
16. S. A. Shmakov, K. S. Makarova, Y. I. Wolf, K. V. Severinov, E. V. Koonin, Systematic prediction of genes functionally linked to CRISPR-Cas systems by gene neighborhood analysis. Proc Natl Acad Sci USA 115, E5307-E5316 (2018).
17. S. A. Shah et al., Comprehensive search for accessory proteins encoded with archaeal and bacterial type III CRISPR-cas gene cassettes reveals 39 new cas gene families. RNA Biol, 1-13 (2018).
18. K. S. Makarova, V. Anantharaman, N. V. Grishin, E. V. Koonin, L. Aravind, CARF and WYL domains: ligand-binding regulators of prokaryotic defense systems. Front Genet 5, 102 (2014).
19. S. A. McMahon et al., Structure and mechanism of a Type III CRISPR defence DNA nuclease activated by cyclic oligoadenylate. Nat Commun 11, 500 (2020).
20. J. Kosinski, M. Feder, J. M. Bujnicki, The PD-(D/E)XK superfamily revisited: identification of new members among proteins involved in DNA metabolism and functional predictions for domains of (hitherto) unknown function. BMC Bioinformatics 6, 172 (2005).
21. K. H. Maslowska, K. Makiela-Dzbenska, I. J. Fijalkowska, The SOS system: A complex and tightly regulated response to DNA damage. Environ Mol Mutagen 60, 368-384 (2019).
22. S. Horinouchi, B. Weisblum, Nucleotide sequence and functional map of pC194, a plasmid that specifies inducible chloramphenicol resistance. J. Bacteriol. 150, 815-825 (1982).
23. B. N. Kreiswirth et al., The toxic shock syndrome exotoxin structural gene is not detectably transmitted by a prophage. Nature 305, 709-712 (1983).
24. R. T. Cirz et al., Complete and SOS-mediated response of Staphylococcus aureus to the antibiotic ciprofloxacin. J. Bacteriol. 189, 531-539 (2007).
25. J. W. Modell, W. Jiang, L. A. Marraffini, CRISPR-Cas systems exploit viral DNA injection to establish and maintain adaptive immunity. Nature 544, 101-104 (2017).
26. G. W. Goldberg, W. Jiang, D. Bikard, L. A. Marraffini, Conditional tolerance of temperate phages via transcription-dependent CRISPR-Cas targeting. Nature 514, 633-637 (2014).
27. J. S. Athukoralage, C. Rouillon, S. Graham, S. Gruschow, M. F. White, Ring nucleases deactivate type III CRISPR ribonucleases by degrading cyclic oligoadenylate. Nature, (2018).
28. R. K. Lau et al., Structure and Mechanism of a Cyclic Trinucleotide-Activated Bacterial Endonuclease Mediating Bacteriophage Immunity. Mol. Cell 77, 723-733 e726 (2020).
29. A. J. Meeske, S. Nakandakari-Higa, L. A. Marraffini, Cas13-induced cellular dormancy prevents the rise of CRISPR-resistant bacteriophage. Nature 570, 241-245 (2019).
30. P. Wawrzyniak, G. Plucienniczak, D. Bartosik, The Different Faces of Rolling-Circle Replication and Its Multifunctional Initiator Proteins. Front Microbiol 8, 2353 (2017).
31. W. Kabsch, Xds. Acta Crystallogr D Biol Crystallogr 66, 125-132 (2010).
32. A. J. McCoy et al., Phaser crystallographic software. J Appl Crystallogr 40, 658-674 (2007).
33. P. D. Adams et al., PHENIX: a comprehensive Python-based system for macromolecular structure solution. Acta Crystallogr D Biol Crystallogr 66, 213-221 (2010).
34. P. Emsley, B. Lohkamp, W. G. Scott, K. Cowtan, Features and development of Coot. Acta Crystallogr D Biol Crystallogr 66, 486-501 (2010).
35. P. V. Afonine et al., Towards automated crystallographic structure refinement with phenix.refine. Acta Crystallogr D Biol Crystallogr 68, 352-367 (2012).
36. T. D. Goddard et al., UCSF ChimeraX: Meeting modern challenges in visualization and analysis. Protein Sci. 27, 14-25 (2018).
37. T. Theis, R. A. Skurray, M. H. Brown, Identification of suitable internal controls to study expression of a Staphylococcus aureus multidrug resistance system by quantitative real-time PCR. J. Microbiol. Methods 70, 355-362 (2007).

38. G. E. Crooks, G. Hon, J. M. Chandonia, S. E. Brenner, WebLogo: a sequence logo generator. Genome Res. 14, 1188-1190 (2004).

39. M. Kearse et al., Geneious Basic: an integrated and extendable desktop software platform for the organization and analysis of sequence data. Bioinformatics 28, 1647-1649 (2012).

40. A. Dobin et al., STAR: ultrafast universal RNA-seq aligner. Bioinformatics 29, 15-21 (2013).

Although the present disclosure has been described using specific embodiments and examples, routine modifications will be apparent to those skilled in the art and such modifications are intended to be within the scope of the disclosure and the claims.

What is claimed is:

1. A method for detecting a target RNA, wherein said method comprises (i) contacting a sample containing a target RNA with a protein that comprises SEQ ID NO: 1, a protein that comprises SEQ ID NO: 3, a guide RNA that is complementary to said target RNA and forms a complex with the protein that comprises SEQ ID NO: 3, and either a reporter single stranded DNA (ssDNA) or a reporter single stranded RNA (ssRNA), and (ii) detecting cleavage of the reporter ssDNA or the reporter RNA, wherein detection of said cleavage indicates the presence of the target RNA in the sample.

2. The method of claim 1, wherein the target RNA comprises a viral mRNA, a viral genomic RNA, a viral subgenomic RNA, or a combination thereof.

* * * * *

```
                        SEQUENCE LISTING

<160> NUMBER OF SEQ ID NOS: 55

<210> SEQ ID NO 1
<211> LENGTH: 373
<212> TYPE: PRT
<213> ORGANISM: Treponema succinifaciens

<400> SEQUENCE: 1

Met Lys Glu Thr Ile Leu Val Asn Leu Val Ser Glu Gln Thr Ile Pro
1               5                   10                  15

Asn Val Gln Phe Ile Lys Trp Tyr Phe Asn Lys Lys Gln Thr Pro Met
                20                  25                  30

Lys Ile Leu Leu Val Ser Thr Lys Glu Met Glu Gln Lys Glu Lys Ser
            35                  40                  45

Leu Phe Ile Lys Asn Ala Leu His Phe Ser Asp Ser Phe Val Glu Trp
        50                  55                  60

Glu Thr Ile His Thr Asp Gly Asn Asp Ile Ser Lys Thr Glu Asn Ile
65                  70                  75                  80

Leu Thr Asp Tyr Phe Arg Asp Asn Glu Tyr Lys Asn Ile Ile Val Asn
                85                  90                  95

Ile Thr Gly Gly Thr Lys Ile Met Ser Leu Ala Ala Phe Asp Phe Phe
                100                 105                 110

Asn Asn Lys Pro Asn Thr Glu Ile Phe Tyr Gln Pro Ile Gly Lys Glu
            115                 120                 125

Leu Gln Glu Leu Tyr Pro Asn Lys Gln Lys Tyr Asp Met Phe Glu Val
        130                 135                 140

Leu Ser Leu Lys Glu Tyr Leu Asp Ala His Gly Ile Ser Tyr Lys Tyr
145                 150                 155                 160

Asp Asn Glu Cys Val Lys Asp Trp Asn Tyr Asn Lys Thr Val Tyr Asp
                165                 170                 175

Leu Cys Val Ala Asp Asn Arg Glu Leu Ile Lys Gly Met Ile Ala Leu
                180                 185                 190

Gln Asn Asn Ser Tyr Phe Asn Asn Val Tyr Lys Arg Lys Asp Phe Leu
            195                 200                 205

Asp Phe Thr Gln Ile Glu Glu Glu Lys Phe Ile Ala Ile Asn His Pro
        210                 215                 220

Ala Ala Thr Lys Glu Asn Met Ile Lys Ile Leu Gln Ile Phe Gly Phe
225                 230                 235                 240

Asp Val Ser Arg Ile Glu His Lys His Ile Arg Tyr Ile Thr Gly Gly
                245                 250                 255

Trp Phe Glu Glu Tyr Val Tyr Gln Lys Ile Cys Asn Glu Tyr His Asn
                260                 265                 270

Val Asp Glu Lys Asn Val Ala Leu Asn Val Thr Ile Gln Lys Gly Asn
            275                 280                 285

Asp Lys Asn Glu Leu Asp Val Ile Tyr Leu Asp Lys Asp Asn Lys Leu
        290                 295                 300

His Val Ile Glu Cys Lys Ser Phe Val Asp Gly Asn Glu Gly Asn Arg
305                 310                 315                 320
```

-continued

```
Val Leu Asn Asp Ala Leu Tyr Lys Leu Gln Ala Ile Ile Lys Ser Lys
                325                 330                 335

Phe Gly Leu Tyr Val Lys Gln His Leu Tyr Thr Lys Ser Ile Ile Glu
                340                 345                 350

Lys Glu Thr Pro Leu Asn Arg Ala Lys Glu Phe Gly Ile Asp Ile Lys
            355                 360                 365

Asp Gly Thr Gln Leu
        370
```

```
<210> SEQ ID NO 2
<211> LENGTH: 1122
<212> TYPE: DNA
<213> ORGANISM: Treponema succinifaciens

<400> SEQUENCE: 2
atgaaagaga ctattttggt taacttggtt agtgagcaaa caattcctaa tgtacaattt        60
atcaagtggt actttaataa aaagcaaaca ccaatgaaga tattgttagt gagtactaag       120
gagatggaac agaaagaaaa atcattgttc atcaagaacg ctttacactt ttcagattca       180
ttcgtggagt gggagacaat tcacactgac ggaaacgaca tatcaaagac agaaaatatt       240
ttgacagact atttcagaga taatgaatac aaaaatataa tagttaatat tacgggcggt       300
acaaagatca tgtctttagc agcatttgat ttctttaata caaaacctaa cacagagata       360
ttctaccaac ctataggtaa agaattgcag gagttatacc caaataagca aaagtacgac       420
atgttcgaag tgttatcttt aaaggaatat ttggatgcgc atggtattag ttataaatac       480
gataacgagt gtgtcaaaga ctggaactat aataagacgg tatatgattt gtgcgttgcg       540
gacaatcgtg aattaataaa gggcatgatc gctttgcaga caactcata tttcaacaat        600 gtatataagc gaaaagattt tttagacttt actcagattg aggaggagaa gttcattgct       660
atcaatcatc cagcggctac aaaggagaat atgattaaga tcttacaaat atttggattt       720
gatgttagtc gaattgagca caagcacatc cgttatataa ctggcggttg gttcgaggag       780
tatgtatatc agaaaatttg caatgaatac cataacgtcg atgaaaagaa cgtagcgtta       840
aacgttacaa ttcagaaggg aaatgacaaa acgagttgg atgttatcta cttggacaaa        900
gacaataagt tacacgtgat agaatgtaag agtttcgtcg atggaaacga aggcaacaga       960
gtattgaacg acgcgttata taagttacaa gcgatcatca gagtaagtt cggattatat       1020 gtaaagcaac acttgtatac gaaaagtatt atagaaaaag aaactccatt gaacagagct      1080
aaagagtttg gaattgacat taaagacggt acacaattat ga                         1122
```

```
<210> SEQ ID NO 3
<211> LENGTH: 757
<212> TYPE: PRT
<213> ORGANISM: Artificial Sequence
<220> FEATURE:
<223> OTHER INFORMATION: Representative Cas10 amino acid sequence

<400> SEQUENCE: 3

Met Asn Lys Lys Asn Ile Leu Met Tyr Gly Ser Leu Leu His Asp Ile
1               5                   10                  15

Gly Lys Ile Ile Tyr Arg Ser Gly Asp His Thr Phe Ser Arg Gly Thr
                20                  25                  30

His Ser Lys Leu Gly His Gln Phe Leu Ser Gln Phe Ser Glu Phe Lys
            35                  40                  45

Asp Asn Glu Val Leu Asp Asn Val Ala Tyr His His Tyr Lys Glu Leu
```

-continued

```
            50                  55                  60

Ala Lys Ala Asn Leu Asp Asn Asp Asn Thr Ala Tyr Ile Thr Tyr Ile
65                  70                  75                  80

Ala Asp Asn Ile Ala Ser Gly Ile Asp Arg Arg Asp Ile Ile Glu Glu
                85                  90                  95

Gly Asp Glu Glu Tyr Glu Lys Gln Leu Phe Asn Phe Asp Lys Tyr Thr
                100                 105                 110

Pro Leu Tyr Ser Val Phe Asn Ile Val Asn Ser Glu Lys Leu Lys Gln
            115                 120                 125

Thr Asn Gly Lys Phe Lys Phe Ser Asn Glu Ser Asn Ile Glu Tyr Pro
            130                 135                 140

Lys Thr Glu Asn Ile Gln Tyr Ser Ser Gly Asn Tyr Thr Thr Leu Met
145                 150                 155                 160

Lys Asp Met Ser His Asp Leu Glu His Lys Leu Ser Ile Lys Glu Gly
                165                 170                 175

Thr Phe Pro Ser Leu Leu Gln Trp Thr Glu Ser Leu Trp Gln Tyr Val
                180                 185                 190

Pro Ser Ser Thr Asn Lys Asn Gln Leu Ile Asp Ile Ser Leu Tyr Asp
            195                 200                 205

His Ser Arg Ile Thr Cys Ala Ile Ala Ser Cys Ile Phe Asp Tyr Leu
        210                 215                 220

Asn Glu Asn Asn Ile His Asn Tyr Lys Asp Glu Leu Phe Ser Lys Tyr
225                 230                 235                 240

Glu Asn Thr Lys Ser Phe Tyr Gln Lys Glu Ala Phe Leu Leu Leu Ser
                245                 250                 255

Met Asp Met Ser Gly Ile Gln Asp Phe Ile Tyr Asn Ile Ser Gly Ser
                260                 265                 270

Lys Ala Leu Lys Ser Leu Arg Ser Arg Ser Phe Tyr Leu Glu Leu Met
                275                 280                 285

Leu Glu Val Ile Val Asp Gln Leu Leu Glu Arg Leu Glu Leu Ala Arg
        290                 295                 300

Ala Asn Leu Leu Tyr Thr Gly Gly Gly His Ala Tyr Leu Leu Val Ser
305                 310                 315                 320

Asn Thr Asp Lys Val Lys Lys Lys Ile Thr Gln Phe Asn Asn Glu Leu
                325                 330                 335

Lys Lys Trp Phe Met Ser Glu Phe Thr Thr Asp Leu Ser Leu Ser Met
                340                 345                 350

Ala Phe Glu Lys Cys Ser Gly Asp Asp Leu Met Asn Thr Ser Gly Asn
            355                 360                 365

Tyr Arg Thr Ile Trp Arg Asn Val Ser Ser Lys Leu Ser Asp Ile Lys
        370                 375                 380

Ala His Lys Tyr Ser Ala Glu Asp Ile Leu Lys Leu Asn His Phe His
385                 390                 395                 400

Ser Tyr Gly Asp Arg Glu Cys Lys Glu Cys Leu Arg Ser Asp Ile Asp
                405                 410                 415

Ile Asn Asp Asp Gly Leu Cys Ser Ile Cys Glu Gly Ile Ile Asn Ile
                420                 425                 430

Ser Asn Asp Leu Arg Asp Lys Ser Phe Phe Val Leu Ser Glu Thr Gly
            435                 440                 445

Lys Leu Lys Met Pro Phe Asn Lys Phe Ile Ser Val Ile Asp Tyr Glu
        450                 455                 460

Glu Ala Glu Met Leu Val Gln Asn Asn Asn Gln Val Arg Ile Tyr Ser
465                 470                 475                 480
```

-continued

```
Lys Asn Lys Pro Tyr Ile Gly Ile Gly Ile Ser Thr Asn Leu Trp Met
                485             490             495

Cys Asp Tyr Asp Tyr Ala Ser Gln Asn Gln Asp Met Arg Glu Lys Gly
                500             505             510

Ile Gly Ser Tyr Val Asp Arg Glu Glu Gly Val Lys Arg Leu Gly Val
                515             520             525

Val Arg Ala Asp Ile Asp Asn Leu Gly Ala Thr Phe Ile Ser Gly Ile
        530             535             540

Pro Glu Lys Tyr Asn Ser Ile Ser Arg Thr Ala Thr Leu Ser Arg Gln
545             550             555             560

Leu Ser Leu Phe Phe Lys Tyr Glu Leu Asn His Leu Leu Glu Asn Tyr
                565             570             575

Gln Ile Thr Ala Ile Tyr Ser Gly Gly Asp Asp Leu Phe Leu Ile Gly
                580             585             590

Ala Trp Asp Asp Ile Ile Glu Ala Ser Ile Tyr Ile Asn Asp Lys Phe
        595             600             605

Lys Glu Phe Thr Leu Asp Lys Leu Thr Leu Ser Ala Gly Val Gly Met
        610             615             620

Phe Ser Gly Lys Tyr Pro Val Ser Lys Met Ala Phe Glu Thr Gly Arg
625             630             635             640

Leu Glu Glu Ala Ala Lys Thr Gly Glu Lys Asn Gln Ile Ser Leu Trp
                645             650             655

Leu Gln Glu Lys Val Tyr Asn Trp Asp Glu Phe Lys Lys Asn Ile Leu
                660             665             670

Glu Glu Lys Leu Leu Val Leu Gln Gln Gly Phe Ser Gln Thr Asp Glu
                675             680             685

His Gly Lys Ala Phe Ile Tyr Lys Met Leu Ala Leu Leu Arg Asn Asn
        690             695             700

Glu Ala Ile Asn Ile Ala Arg Leu Ala Tyr Leu Leu Ala Arg Ser Lys
705             710             715             720

Met Asn Glu Asp Phe Thr Ser Lys Ile Phe Asn Trp Ala Gln Asn Asp
                725             730             735

Lys Asp Lys Asn Gln Leu Ile Thr Ala Leu Glu Tyr Tyr Ile Tyr Gln
                740             745             750

Ile Arg Glu Ala Asp
        755
```

```
<210> SEQ ID NO 4
<211> LENGTH: 2274
<212> TYPE: DNA
<213> ORGANISM: Artificial Sequence
<220> FEATURE:
<223> OTHER INFORMATION: Representative Cas10 nucleotide coding sequence

<400> SEQUENCE: 4
atgaataaaa aaaatatatt aatgtatggc tctttattac atgatatagg gaaaattata      60
tatcgaagtg gtgatcatac attttcaaga ggtacgcatt caaaattagg tcatcaattt     120
ttgtcccaat tttcagaatt taaagacaac gaagtgcttg ataacgttgc ttatcatcat     180
tacaaagaac tcgcaaaagc taatttagat aatgataata cagcttatat tacctatatt     240
gcggataata ttgcgagtgg tattgataga agagatatta tagaagaagg cgatgaagaa     300
tacgaaaaac aactatttaa ttttgataaa tatacaccgc tatatagtgt gtttaatatt     360
gtgaattctg aaaaattgaa acaaacaaac gggaagttta aattttctaa tgaaagtaat     420
```

-continued

```
attgaatatc ctaaaactga aaacattcaa tattcaagtg gaaattatac aacattaatg      480
aaagatatga gtcatgattt agagcacaaa ttaagtatta aagaaggtac atttccttca      540
ttattacaat ggacggaaag tctatggcaa tatgtaccta gttcgacaaa taaaaaccaa      600
ttaattgata tttctcttta tgatcatagt cgtattacat gtgccatcgc cagttgtata      660
tttgattatt taaatgaaaa taacatacat aattacaaag atgaattgtt ctcaaagtat      720
gaaaatacca aatcatttta tcaaaaagaa gctttttta  tacttagtat ggatatgagt      780
ggtattcaag attttattta caatataagc ggttctaaag cattaaagag tctaagatct      840
cgtagttttt atttagaact catgcttgaa gtaatcgttg atcaattatt agaaagatta      900
gaattagcac gagcaaatct tttgtataca ggtggtggcc atgcttattt attagtgtct      960
aatactgata aagtgaagaa aaaaataact caatttaata atgaattaaa aaaatggttt     1020
atgtcagaat ttactacaga tctttcatta tcaatggctt ttgaaaaatg tagtggcgat     1080
gatttaatga atacaagtgg taattataga actatttggc gtaatgttag cagcaaactt     1140
tctgatatta aagcgcataa atattccgcg gaagatatat taaaattaaa tcattttcat     1200
tcgtatggag atcgggaatg taaagaatgt ttaagaagtg acatagatat taatgatgat     1260
ggactatgta gtatatgtga aggaattatt aatatatcaa atgatttaag agataaatca     1320
ttctttgtac tgtcagaaac tggaaaatta aaaatgccat tcaataaatt tatatcggtt     1380
attgattatg aagaggcaga aatgttagta caaaataata atcaagttcg tatttacagt     1440
aaaaataaac catatatagg cataggaata tcaacaaatt tatggatgtg tgattacgac     1500
tatgctagtc aaaatcaaga tatgagagaa aaaggtattg gaagttatgt agatagagaa     1560
gaaggggtta agcgtttagg cgtggtacgt gccgatatag ataatctcgg tgctacattt     1620
atatctggaa ttccagaaaa atataattca atttcaagaa cagctacatt gtctcgtcaa     1680
ttatcattat ttttttaaata cgaattaaat catttattag aaaattatca aattactgct     1740
atatattcag gcggtgacga tttattttta atcggtgcat gggatgacat tatagaagca     1800
agcatttata taaatgacaa atttaaagag tttactcttg ataaactaac attgtctgcc     1860
ggggttggaa tgtttagtgg taagtaccca gtttctaaaa tggcttttga gacaggacga     1920
cttgaagaag cggctaagac tggtgaaaaa aatcagatat ctctttggtt acaagaaaaa     1980
gtatataact gggatgagtt taaaaagaat atccttagaag aaaaacttct cgttttacaa     2040
cagggttttt ctcaaacaga tgaacacggg aaagccttca tttataaaat gctcgcttta     2100
ctgagaaata atgaagctat taatattgct cgtttagctt acttattagc aagaagcaag     2160
atgaatgagg attttacgtc taaaattttt aattgggctc aaaacgacaa agataaaaat     2220
caattaatta cagcgttaga gtattatatt tatcaaataa gggaggctga ttga           2274
```

<210> SEQ ID NO 5
<211> LENGTH: 232
<212> TYPE: PRT
<213> ORGANISM: Listeriaphage (PhiLS46)

<400> SEQUENCE: 5

```
Met Ile Tyr Tyr Ile Lys Asp Leu Lys Val Lys Gly Lys Ile Phe Glu
1               5                   10                  15

Asn Leu Met Asn Lys Glu Ala Val Glu Gly Leu Ile Thr Phe Leu Lys
            20                  25                  30

Lys Ala Glu Phe Glu Ile Tyr Ser Arg Glu Asn Tyr Ser Lys Tyr Asn
        35                  40                  45
```

-continued

```
Lys Trp Phe Glu Met Trp Lys Ser Pro Thr Ser Ser Leu Val Phe Trp
    50              55                  60

Lys Asn Tyr Ser Phe Arg Cys His Leu Leu Phe Val Ile Glu Lys Asp
65              70                  75                  80

Gly Glu Cys Leu Gly Ile Pro Ala Ser Val Phe Glu Ser Val Leu Gln
                85                  90                  95

Ile Tyr Leu Ala Asp Pro Phe Ala Pro Asp Thr Lys Glu Leu Phe Val
            100                 105                 110

Glu Val Cys Asn Leu Tyr Glu Cys Leu Ala Asp Val Thr Val Val Glu
            115                 120                 125

His Phe Glu Ala Glu Glu Ser Ala Trp His Lys Leu Thr His Asn Glu
    130                 135                 140

Thr Glu Val Ser Lys Arg Val Tyr Ser Lys Asp Asp Asp Glu Leu Leu
145                 150                 155                 160

Lys Tyr Ile Pro Glu Phe Leu Asp Thr Ile Ala Thr Asn Lys Lys Ser
                165                 170                 175

Gln Lys Tyr Asn Gln Ile Gln Gly Lys Ile Gln Glu Ile Asn Lys Glu
            180                 185                 190

Ile Ala Thr Leu Tyr Glu Ser Ser Glu Asp Tyr Ile Phe Thr Glu Tyr
            195                 200                 205

Val Ser Asn Leu Tyr Arg Glu Ser Ala Lys Leu Glu Gln His Ser Lys
    210                 215                 220

Gln Ile Leu Lys Glu Glu Leu Asn
225                 230

<210> SEQ ID NO 6
<211> LENGTH: 24
<212> TYPE: DNA
<213> ORGANISM: Artificial Sequence
<220> FEATURE:
<223> OTHER INFORMATION: oligo used in cloning

<400> SEQUENCE: 6
catattgcct gatgaagtga atag                                          24

<210> SEQ ID NO 7
<211> LENGTH: 24
<212> TYPE: DNA
<213> ORGANISM: Artificial Sequence
<220> FEATURE:
<223> OTHER INFORMATION: oligo used in cloning

<400> SEQUENCE: 7
ctattcactt catcaggcaa tatg                                          24

<210> SEQ ID NO 8
<211> LENGTH: 39
<212> TYPE: DNA
<213> ORGANISM: Artificial Sequence
<220> FEATURE:
<223> OTHER INFORMATION: oligo used in cloning

<400> SEQUENCE: 8
gaacagtgtc taacaactgc aattcactaa atgctgtaa                          39

<210> SEQ ID NO 9
<211> LENGTH: 39
<212> TYPE: DNA
<213> ORGANISM: Artificial Sequence
<220> FEATURE:
<223> OTHER INFORMATION: oligo used in cloning
```

<400> SEQUENCE: 9
gatcttacag catttagtga attgcagttg ttagacact                                      39

<210> SEQ ID NO 10
<211> LENGTH: 34
<212> TYPE: DNA
<213> ORGANISM: Artificial Sequence
<220> FEATURE:
<223> OTHER INFORMATION: oligo used in cloning

<400> SEQUENCE: 10
atgataaata aaattacagt agagttagac ttgc                                           34

<210> SEQ ID NO 11
<211> LENGTH: 31
<212> TYPE: DNA
<213> ORGANISM: Artificial Sequence
<220> FEATURE:
<223> OTHER INFORMATION: oligo used in cloning

<400> SEQUENCE: 11
tatagcacct cattatttaa ctcttgaaaa c                                              31

<210> SEQ ID NO 12
<211> LENGTH: 54
<212> TYPE: DNA
<213> ORGANISM: Artificial Sequence
<220> FEATURE:
<223> OTHER INFORMATION: oligo used in cloning

<400> SEQUENCE: 12
caagagttaa ataatgaggt gctataatga aagagactat tttggttaac ttgg                     54

<210> SEQ ID NO 13
<211> LENGTH: 70
<212> TYPE: DNA
<213> ORGANISM: Artificial Sequence
<220> FEATURE:
<223> OTHER INFORMATION: oligo used in cloning

<400> SEQUENCE: 13
ctaactctac tgtaatttta tttatcatat gtatatctcc ttctcataat tgtgtaccgt              60
ctttaatgtc                                                                     70

<210> SEQ ID NO 14
<211> LENGTH: 41
<212> TYPE: DNA
<213> ORGANISM: Artificial Sequence
<220> FEATURE:
<223> OTHER INFORMATION: oligo used in cloning

<400> SEQUENCE: 14
gttacacgtg atagcatgtg ctagtttcgt cgatggaaac g                                   41

<210> SEQ ID NO 15
<211> LENGTH: 45
<212> TYPE: DNA
<213> ORGANISM: Artificial Sequence
<220> FEATURE:
<223> OTHER INFORMATION: oligo used in cloning

<400> SEQUENCE: 15
gacgaaacta gcacatgcta tcacgtgtaa cttattgtct ttgtc                               45

-continued

```
<210> SEQ ID NO 16
<211> LENGTH: 20
<212> TYPE: DNA
<213> ORGANISM: Artificial Sequence
<220> FEATURE:
<223> OTHER INFORMATION: oligo used in cloning

<400> SEQUENCE: 16
gatccggctg ctaacaaagc                                              20

<210> SEQ ID NO 17
<211> LENGTH: 41
<212> TYPE: DNA
<213> ORGANISM: Artificial Sequence
<220> FEATURE:
<223> OTHER INFORMATION: oligo used in cloning

<400> SEQUENCE: 17
atgtatatct ccttcttaaa gttaaacaaa attatttcta g                      41

<210> SEQ ID NO 18
<211> LENGTH: 55
<212> TYPE: DNA
<213> ORGANISM: Artificial Sequence
<220> FEATURE:
<223> OTHER INFORMATION: oligo used in cloning

<400> SEQUENCE: 18
gtttaacttt aagaaggaga tatacatatg aaagagacta ttttggttaa cttgg        55

<210> SEQ ID NO 19
<211> LENGTH: 49
<212> TYPE: DNA
<213> ORGANISM: Artificial Sequence
<220> FEATURE:
<223> OTHER INFORMATION: oligo used in cloning

<400> SEQUENCE: 19
cgggctttgt tagcagccgg atcttagtga tggtgatggt gatgtcctg              49

<210> SEQ ID NO 20
<211> LENGTH: 33
<212> TYPE: DNA
<213> ORGANISM: Artificial Sequence
<220> FEATURE:
<223> OTHER INFORMATION: oligo used in cloning

<400> SEQUENCE: 20
caacaaaagt atttaaactt tcttttaaga ctc                               33

<210> SEQ ID NO 21
<211> LENGTH: 56
<212> TYPE: DNA
<213> ORGANISM: Artificial Sequence
<220> FEATURE:
<223> OTHER INFORMATION: oligo used in cloning

<400> SEQUENCE: 21
gaaagtttaa atactttgt tgccaatgtc attcacctac ttaattttaa gatttg        56

<210> SEQ ID NO 22
<211> LENGTH: 31
<212> TYPE: DNA
<213> ORGANISM: Artificial Sequence
<220> FEATURE:
<223> OTHER INFORMATION: oligo used in cloning
```

-continued

<400> SEQUENCE: 22
aacaattcct aatgtacaat ttatcaagtg g                                    31

<210> SEQ ID NO 23
<211> LENGTH: 55
<212> TYPE: DNA
<213> ORGANISM: Artificial Sequence
<220> FEATURE:
<223> OTHER INFORMATION: oligo used in cloning

<400> SEQUENCE: 23
gataaattgt acattaggaa ttgttgcctc actaaccaag ttaaccaaaa tagtc          55

<210> SEQ ID NO 24
<211> LENGTH: 30
<212> TYPE: DNA
<213> ORGANISM: Artificial Sequence
<220> FEATURE:
<223> OTHER INFORMATION: oligo used in cloning

<400> SEQUENCE: 24
gagcaaacaa ttcctaatgt acaatttatc                                      30

<210> SEQ ID NO 25
<211> LENGTH: 53
<212> TYPE: DNA
<213> ORGANISM: Artificial Sequence
<220> FEATURE:
<223> OTHER INFORMATION: oligo used in cloning

<400> SEQUENCE: 25
gtacattagg aattgtttgc tctgcaacca agttaaccaa aatagtctct ttc            53

<210> SEQ ID NO 26
<211> LENGTH: 27
<212> TYPE: DNA
<213> ORGANISM: Artificial Sequence
<220> FEATURE:
<223> OTHER INFORMATION: oligo used in cloning

<400> SEQUENCE: 26
atggaacaga agaaaaatc attgttc                                          27

<210> SEQ ID NO 27
<211> LENGTH: 57
<212> TYPE: DNA
<213> ORGANISM: Artificial Sequence
<220> FEATURE:
<223> OTHER INFORMATION: oligo used in cloning

<400> SEQUENCE: 27
caatgatttt tctttctgtt ccattgcctt agtactcact aacaatatct tcattgg        57

<210> SEQ ID NO 28
<211> LENGTH: 30
<212> TYPE: DNA
<213> ORGANISM: Artificial Sequence
<220> FEATURE:
<223> OTHER INFORMATION: oligo used in cloning

<400> SEQUENCE: 28
gaacagaaag aaaaatcatt gttcatcaag                                      30

<210> SEQ ID NO 29

-continued

```
<211> LENGTH: 60
<212> TYPE: DNA
<213> ORGANISM: Artificial Sequence
<220> FEATURE:
<223> OTHER INFORMATION: oligo used in cloning

<400> SEQUENCE: 29
gaacaatgat ttttctttct gttctgcctc cttagtactc actaacaata tcttcattgg          60

<210> SEQ ID NO 30
<211> LENGTH: 26
<212> TYPE: DNA
<213> ORGANISM: Artificial Sequence
<220> FEATURE:
<223> OTHER INFORMATION: oligo used in cloning

<400> SEQUENCE: 30
aggtaaagaa ttgcaggagt tatacc                                              26

<210> SEQ ID NO 31
<211> LENGTH: 54
<212> TYPE: DNA
<213> ORGANISM: Artificial Sequence
<220> FEATURE:
<223> OTHER INFORMATION: oligo used in cloning

<400> SEQUENCE: 31
gtataactcc tgcaattctt tacctgcagg ttggtagaat atctctgtgt tagg               54

<210> SEQ ID NO 32
<211> LENGTH: 26
<212> TYPE: DNA
<213> ORGANISM: Artificial Sequence
<220> FEATURE:
<223> OTHER INFORMATION: oligo used in cloning

<400> SEQUENCE: 32
gtaaagcaac acttgtatac gaaaag                                              26

<210> SEQ ID NO 33
<211> LENGTH: 55
<212> TYPE: DNA
<213> ORGANISM: Artificial Sequence
<220> FEATURE:
<223> OTHER INFORMATION: oligo used in cloning

<400> SEQUENCE: 33
cttttcgtat acaagtgttg ctttactgct aatccgaact tactcttgat gatcg             55

<210> SEQ ID NO 34
<211> LENGTH: 26
<212> TYPE: DNA
<213> ORGANISM: Artificial Sequence
<220> FEATURE:
<223> OTHER INFORMATION: oligo used in cloning

<400> SEQUENCE: 34
atgtaagagt ttcgtcgatg gaaacg                                              26

<210> SEQ ID NO 35
<211> LENGTH: 51
<212> TYPE: DNA
<213> ORGANISM: Artificial Sequence
<220> FEATURE:
<223> OTHER INFORMATION: oligo used in cloning

<400> SEQUENCE: 35
```

-continued

--- ccatcgacga aactcttaca tgctatcacg tgtaacttat tgtctttgtc c                51

<210> SEQ ID NO 36
<211> LENGTH: 22
<212> TYPE: DNA
<213> ORGANISM: Artificial Sequence
<220> FEATURE:
<223> OTHER INFORMATION: oligo used in cloning

<400> SEQUENCE: 36
aatgtaagag tttcgtcgat gg                                                22

<210> SEQ ID NO 37
<211> LENGTH: 51
<212> TYPE: DNA
<213> ORGANISM: Artificial Sequence
<220> FEATURE:
<223> OTHER INFORMATION: oligo used in cloning

<400> SEQUENCE: 37
ccatcgacga aactcttaca ttgtatcacg tgtaacttat tgtctttgtc c                51

<210> SEQ ID NO 38
<211> LENGTH: 25
<212> TYPE: DNA
<213> ORGANISM: Artificial Sequence
<220> FEATURE:
<223> OTHER INFORMATION: oligo used in cloning

<400> SEQUENCE: 38
caacctatag gtaaagaatt gcagg                                             25

<210> SEQ ID NO 39
<211> LENGTH: 60
<212> TYPE: DNA
<213> ORGANISM: Artificial Sequence
<220> FEATURE:
<223> OTHER INFORMATION: oligo used in cloning

<400> SEQUENCE: 39
caattcttta cctataggtt gtgcgaatat ctctgtgtta ggtttgttat taaagaaatc      60

<210> SEQ ID NO 40
<211> LENGTH: 31
<212> TYPE: DNA
<213> ORGANISM: Artificial Sequence
<220> FEATURE:
<223> OTHER INFORMATION: oligo used in cloning

<400> SEQUENCE: 40
gttatctact tggacaaaga caataagtta c                                      31

<210> SEQ ID NO 41
<211> LENGTH: 46
<212> TYPE: DNA
<213> ORGANISM: Artificial Sequence
<220> FEATURE:
<223> OTHER INFORMATION: oligo used in cloning

<400> SEQUENCE: 41
gtctttgtcc aagtagataa ctgccaactc gtttttgtca tttccc                      46

<210> SEQ ID NO 42
<211> LENGTH: 30
<212> TYPE: DNA

-continued

```
<213> ORGANISM: Artificial Sequence
<220> FEATURE:
<223> OTHER INFORMATION: primer

<400> SEQUENCE: 42
gttcagttac attagataat gcgctaggtg                                    30

<210> SEQ ID NO 43
<211> LENGTH: 20
<212> TYPE: DNA
<213> ORGANISM: Artificial Sequence
<220> FEATURE:
<223> OTHER INFORMATION: primer

<400> SEQUENCE: 43
cgataaatgc tgccaccccg                                               20

<210> SEQ ID NO 44
<211> LENGTH: 28
<212> TYPE: DNA
<213> ORGANISM: Artificial Sequence
<220> FEATURE:
<223> OTHER INFORMATION: primer

<400> SEQUENCE: 44
ctgtgacttt accaataact ggcacatg                                      28

<210> SEQ ID NO 45
<211> LENGTH: 27
<212> TYPE: DNA
<213> ORGANISM: Artificial Sequence
<220> FEATURE:
<223> OTHER INFORMATION: primer

<400> SEQUENCE: 45
ctgttcatgg tcacctttca cgtcttg                                       27

<210> SEQ ID NO 46
<211> LENGTH: 30
<212> TYPE: DNA
<213> ORGANISM: Artificial Sequence
<220> FEATURE:
<223> OTHER INFORMATION: primer

<400> SEQUENCE: 46
cgatactata tatgctgaag gacaacgacg                                    30

<210> SEQ ID NO 47
<211> LENGTH: 33
<212> TYPE: DNA
<213> ORGANISM: Artificial Sequence
<220> FEATURE:
<223> OTHER INFORMATION: primer

<400> SEQUENCE: 47
cttgttgttt tttgatctat tgaaattgct ggc                                33

<210> SEQ ID NO 48
<211> LENGTH: 27
<212> TYPE: DNA
<213> ORGANISM: Artificial Sequence
<220> FEATURE:
<223> OTHER INFORMATION: primer

<400> SEQUENCE: 48
cgagtgtttc ttgtattgaa aaggggc                                       27
```

-continued

```
<210> SEQ ID NO 49
<211> LENGTH: 25
<212> TYPE: DNA
<213> ORGANISM: Artificial Sequence
<220> FEATURE:
<223> OTHER INFORMATION: primer

<400> SEQUENCE: 49
gtggtatttc aaacaatcgc gaccc                                         25

<210> SEQ ID NO 50
<211> LENGTH: 25
<212> TYPE: DNA
<213> ORGANISM: Artificial Sequence
<220> FEATURE:
<223> OTHER INFORMATION: oligo used in cloning

<400> SEQUENCE: 50
ggttatacta aaagtcgttt gttgg                                         25

<210> SEQ ID NO 51
<211> LENGTH: 25
<212> TYPE: DNA
<213> ORGANISM: Artificial Sequence
<220> FEATURE:
<223> OTHER INFORMATION: oligo used in cloning

<400> SEQUENCE: 51
ccaacaaacg acttttagta taacc                                         25

<210> SEQ ID NO 52
<211> LENGTH: 22
<212> TYPE: DNA
<213> ORGANISM: Artificial Sequence
<220> FEATURE:
<223> OTHER INFORMATION: primer

<400> SEQUENCE: 52
gtcaatgacc ataacgcaga ag                                            22

<210> SEQ ID NO 53
<211> LENGTH: 23
<212> TYPE: DNA
<213> ORGANISM: Artificial Sequence
<220> FEATURE:
<223> OTHER INFORMATION: primer

<400> SEQUENCE: 53
caatcggtgt tactaaatcc atg                                           23

<210> SEQ ID NO 54
<211> LENGTH: 47
<212> TYPE: DNA
<213> ORGANISM: Artificial Sequence
<220> FEATURE:
<223> OTHER INFORMATION: oligo used in cloning

<400> SEQUENCE: 54
ccgattaaaa ataaagctgc accgcctgaa tatatagcag taatttg                 47

<210> SEQ ID NO 55
<211> LENGTH: 43
<212> TYPE: DNA
<213> ORGANISM: Artificial Sequence
<220> FEATURE:
```

-continued

```
<223> OTHER INFORMATION: oligo used in cloning

<400> SEQUENCE: 55
tattcaggcg gtgcagcttt atttttaatc ggtgcatggg atg                          43
```